US012716877B1

(12) United States Patent
McDaniel

(10) Patent No.: US 12,716,877 B1
(45) Date of Patent: Aug. 25, 2026

(54) AUTOMATED TITRATION TESTING SYSTEM

(71) Applicant: Allexander Michael McDaniel, Snoqualmie, WA (US)

(72) Inventor: Allexander Michael McDaniel, Snoqualmie, WA (US)

( * ) Notice: Subject to any disclaimer, the term of this patent is extended or adjusted under 35 U.S.C. 154(b) by 0 days.

(21) Appl. No.: 19/251,644

(22) Filed: Jun. 26, 2025

Related U.S. Application Data

(60) Provisional application No. 63/664,866, filed on Jun. 27, 2024.

(51) Int. Cl.

| | |
|---|---|
| ***G01N 31/16*** | (2006.01) |
| ***G01N 21/78*** | (2006.01) |
| ***G01N 33/18*** | (2006.01) |
| ***G01N 35/02*** | (2006.01) |

(52) U.S. Cl.
CPC ............. *G01N 31/16* (2013.01); *G01N 21/78* (2013.01); *G01N 33/18* (2013.01); *G01N 35/025* (2013.01)

(58) Field of Classification Search
CPC ........ G01N 31/16; G01N 21/78; G01N 33/18; G01N 35/025
See application file for complete search history.

(56) References Cited

U.S. PATENT DOCUMENTS 3,186,799 A 6/1965 Hach
4,311,586 A * 1/1982 Baldwin ................ B01D 15/08 210/101
4,865,992 A 9/1989 Hach et al.
5,192,509 A 3/1993 Surjaatmadja et al.
(Continued)

FOREIGN PATENT DOCUMENTS

CN 112924494 A * 6/2021 ........... G01N 27/041
CN 114924029 A * 8/2022 ............ G01N 21/78
(Continued)

OTHER PUBLICATIONS https://www.hach.com/. [Date accessed: Sep. 20, 2024].
(Continued)

*Primary Examiner* — Melvin C. Mayes
*Assistant Examiner* — Sophia Y Lyle
(74) *Attorney, Agent, or Firm* — Bold IP PLLC; Houda El-Jarrah

(57) ABSTRACT

A computer implemented system for performing automated titration testing of water samples in order to calculate certain relevant metrics to ensure that the water at the water sites meets the desired standards. A computing device has an testing module that analyzes and produces reports containing data regarding the metrics for samples that have undergone testing using a separate titration device. The titration device includes an automated mobile carousel that holds multiple samples and a reaction chamber with a receptacle configured to receive fluid from the samples. The titration testing device automatically pumps the sample into a sample container held in place in the reaction chamber and pumps an appropriate amount of titrant depending on the metric being tested for so that different titrants are used depending on the metric and detects when the color change/endpoint occurs. Data is collected and reported to the computing device and titration testing module.

9 Claims, 10 Drawing Sheets

(56) References Cited

U.S. PATENT DOCUMENTS

| | | | | |
|---|---|---|---|---|
| 7,153,695 | B2 | 12/2006 | Roeraade et al. | |
| 7,988,916 | B2 | 8/2011 | Bremauer | |
| 8,431,412 | B2 | 4/2013 | Tokhtuev et al. | |
| 8,980,636 | B2 | 3/2015 | Bolduc et al. | |
| 10,150,680 | B1 | 12/2018 | Kurani et al. | |
| 10,287,180 | B1 | 5/2019 | Kurani et al. | |
| 10,871,475 | B2 | 12/2020 | Chamberlain et al. | |
| 11,154,855 | B2 | 10/2021 | Nordman et al. | |
| 11,231,360 | B2 | 1/2022 | Kenowski | |
| 11,397,171 | B2 | 7/2022 | Ryther et al. | |
| 11,454,619 | B2 | 9/2022 | Kraus et al. | |
| 11,833,517 | B2 | 12/2023 | Szpak et al. | |
| 11,885,781 | B2 | 1/2024 | Kathe et al. | |
| 2003/0032195 | A1* | 2/2003 | Roeraade | G01N 31/166 436/51 |
| 2006/0210961 | A1 | 9/2006 | Magnaldo et al. | |
| 2010/0059423 | A1 | 3/2010 | Davis et al. | |
| 2014/0273244 | A1* | 9/2014 | Bolduc | G01N 31/16 436/51 |
| 2019/0201888 | A1* | 7/2019 | Mclntyre | B01L 3/523 |
| 2019/0346414 | A1* | 11/2019 | Ting | G01N 33/18 |
| 2020/0132704 | A1* | 4/2020 | Wang | G01N 31/16 |
| 2023/0393076 | A1 | 12/2023 | Sun et al. | |

FOREIGN PATENT DOCUMENTS

| | | | | | |
|---|---|---|---|---|---|
| CN | 219065394 | U | * | 5/2023 | |
| DE | 102023206987 | A1 | * | 1/2024 | G01N 27/302 |
| JP | 2024001828 | A | * | 1/2024 | |
| WO | WO-2025009538 | A1 | * | 1/2025 | G01N 31/16 |

OTHER PUBLICATIONS

"IK-2000 Series GUARDIAN Boiler Feedwater Analyzer for Dissolved Oxygen + Conductivity + Sulfite + Fluorescein," www.pyxis-lab.com/. https://www.pyxis-lab.com/product/ik-2000-series-guadian-boiler-feedwater-analyzer/ [Date accessed: Sep. 20, 2024].

* cited by examiner 206 (Cavity)
205
118
202
202
202
Sample bottle openings
Sample carousel
116
122
Microcontroller
Stepper motor
120

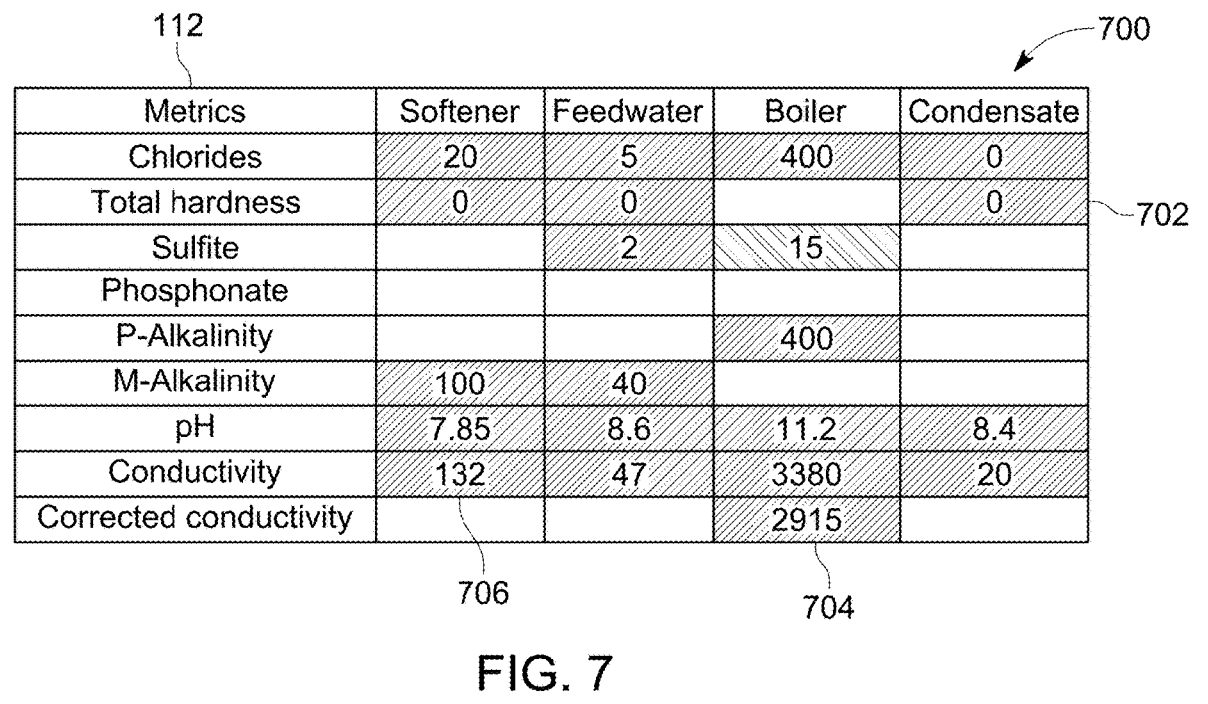

| Metrics | Softener | Feedwater | Boiler | Condensate |
|---|---|---|---|---|
| Chlorides | 20 | 5 | 400 | 0 |
| Total hardness | 0 | 0 | | 0 |
| Sulfite | | 2 | 15 | |
| Phosphonate | | | | |
| P-Alkalinity | | | 400 | |
| M-Alkalinity | 100 | 40 | | |
| pH | 7.85 | 8.6 | 11.2 | 8.4 |
| Conductivity | 132 | 47 | 3380 | 20 |
| Corrected conductivity | | | 2915 | |

FIG. 7

AUTOMATED TITRATION TESTING SYSTEM

CROSS-REFERENCE TO RELATED APPLICATIONS

This non-provisional patent application claims priority to U.S. Provisional Patent Application No. 63/664,866 filed on Jun. 27, 2024, which is incorporated by reference in its entirety.

FIELD OF THE DISCLOSURE

The present invention relates to a system and method for performing automated titrations and data recording to analyze specific water quality parameters for industrial and commercial water treatment facilities.

BACKGROUND

The industrial and commercial water treatment industry provides valuable chemicals for common industrial processes. These chemicals help maximize the life of equipment and also help maintain an energy efficient process. An important part of the job of the chemical applicator person is to test the process water for key analytes in order to ensure that the chemicals are present in the correct concentrations and that they are achieving the desired outcome. The most common way to perform this task is via titrations, manually taking water samples and painstakingly testing each target analyte while recording the data. This approach frequently leads to inaccurate and inconsistent data due to human error; namely the determination of the end point is somewhat subjective and results in variation within the data between individuals. Oftentimes the testing is done by building engineers who have no chemistry background and can be confused by the tests, or they are busy and chose to perform the tests sloppily in order to move on to the next task more quickly. These inherent problems in the current methodology can lead to poor chemical balancing which can result in the loss of expensive equipment or conditions which cause persistent consumption of excess energy.

Furthermore, many facilities operate consistently in an understaffed state, therefore spending up to 1 hour per day testing chemical concentrations in the water is a sore spot for many building operators. Many water treaters recommend testing the water in steam boiler systems and cooling towers daily, which would translate to 360 hours per year of testing, or 9 work weeks per year only performing water testing. The loss of this time has an opportunity cost which results in other urgent tasks being delayed or incomplete. This time spent testing is also significant financially. The average salary of a facilities engineer can range from $60,000-$120,000/yr, so 9 weeks of lost productivity costs $10384-$20769 each year devoted entirely to checking system chemistry.

Accordingly, there is still a great need for a solution which provides consistent reliable data and requires less time of building engineers to perform their required tasks.

SUMMARY

The present description includes non-limiting embodiments for a system for testing water samples. The system may comprise a titration testing device for performing multiple automated titrations. The titration testing device may include a carousel comprising samples held in a plurality of sample bottles. The carousel is movable and/or rotatable, wherein the samples comprise fluid from a test site that needs to be tested for one or more metrics by the performing of the multiple titrations. The titration testing device may further comprise a motor, wherein the motor controls movement of the carousel as well as a reaction chamber, wherein the reaction chamber houses a reaction chamber receptacle configured to receive fluid pumped from the samples stored on the carousel for automatic titration testing to obtain actual measurements for the one or more metrics, wherein the samples in the carousel are configured to be pumped to the reaction chamber receptacle. The titration testing device may further comprise a color sensor and a mixer and in some cases a pH probe and conductivity probe that may also be self-calibrating. The titration testing device may further comprise a titrant delivery mechanism in fluid communication with the reaction chamber and the reaction chamber receptacle. The titration testing device may further comprise indicator dye and one or more pumps. The titration testing device may further comprise a clean water source wherein the clean water source provides water that is pumped to the reaction chamber receptacle before a new titration occurs in the titration reaction receptacle. The titration testing device may further comprise a microcontroller. The titration testing device may further comprise a computing device comprising a titration testing module program, wherein the titration testing module receives data communicated from the titration testing device, wherein the titration testing module is in signal communication with the microcontroller and one or more drivers. The titration testing module comprises interfaces for selecting one or more tests to perform on a particular sample of the samples using the titration testing device to test for one or more metrics. The titration testing module receives data from the titration testing device and stores the data related to the one or more metrics. The titration testing module provides an assembled list of sample test types. A set of pre-determined metrics are associated with each sample test type of the assembled list of sample test types. A may select which metric of the one or more metrics for testing with a particular sample test type for the assembled list of sample test types. The one or more metrics comprise conductivity, pH, p-alkalinity, total hardness, calcium hardness, chloride level, sulfite level, nitrite level, conductivity, corrected conductivity, m-alkalinity, OH-alkalinity, phosphate level, or phosphonate level. A lid assembly may be included wherein a lid is coupled to a tube and a one way check valve and a gasket seal is coupled or attached to a top surface of the lid. The titration testing device may automatically position the lid assembly onto a sample container before pumping sample fluid to the reaction chamber receptacle. An airtight nozzle may be positioned on the gasket seal of the lid. An endpoint is sensed by the color sensor after titration is started. An effluent pump may be included in the titration testing device, wherein an analyte solution stored in the reaction chamber receptacle is pumped out of the reaction chamber receptacle by the effluent pump upon conclusion of testing. The titration testing module provides an interface to select a particular test with a set of pre-determined metrics. The titration testing module produces one or more reports for analysis that contains values and data related to each metric A method for using the titration testing device may further include receiving a request for testing on a computing device, wherein the computing device is in signal communication with the microcontroller of the automatic titration testing device. This may further comprise displaying an interface that is part of a titration testing module configured for selecting a predetermined test from a variety of test options for the samples, wherein the predetermined test comprises one or more metrics that the samples are to be tested for as well as receiving a selection for the predetermined test. The method may further comprise activating a test run for a specific sample container stored on the carousel of the samples. The method may further comprise pumping a known volume of fluid from the specific sample container into the reaction chamber receptacle housed in the reaction chamber. The method may further comprise pumping indicator dye into the reaction chamber receptacle. The method may further comprise, if the predetermined test is configured to cause the required buffer solution to be added to the reaction chamber receptacle, pumping any required buffer solutions into the reaction chamber receptacle. The method may further comprise mixing contents of the reaction chamber receptacle using the mixer. The method may further comprise commencing pumping titrant into the reaction chamber receptacle and measure how much of the titrant is added to the reaction chamber receptacle and activating the color sensor which monitors and detects a color change when an endpoint is reached in the titration process. The method may further comprise upon detecting the endpoint, stopping any further addition of the titrant into the reaction chamber receptacle. The method may further comprise recording a volume of the titrant used to reach the endpoint and applying a relevant formula applicable for calculating and determining data associated with a relevant metric of the one or more metrics from the predetermined test. The method may further comprise recording obtained values for the relevant metric in the titration testing module. The method may further comprise cleaning the reaction chamber receptacle, further comprising, pumping rinse water into the reaction chamber receptacle resulting in waste fluid. The method may further comprise pumping the waste fluid out of the reaction chamber receptacle using an effluent pump. If an additional metric is included in the predetermined test, the method may include beginning another titration to analyze the additional metric and then repeating the steps listed above until all metrics for the pre-determined test are tested and specific measurable values and data are recorded in a tangible, visible manner to the user on an interface of the computing device and an interface of the titration testing module. The method may further comprise providing troubleshooting instructions for correcting a range of fluid held in the test site if the data associated with the relevant metric is not within a recommended range.

Other aspects and advantages of the invention will be apparent from the following description and the appended claims.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

FIG. 7 is an exemplary table or report with readings and data provided from the titration tests performed by the automatic titration testing device.

DETAILED DESCRIPTION

Figure 1:
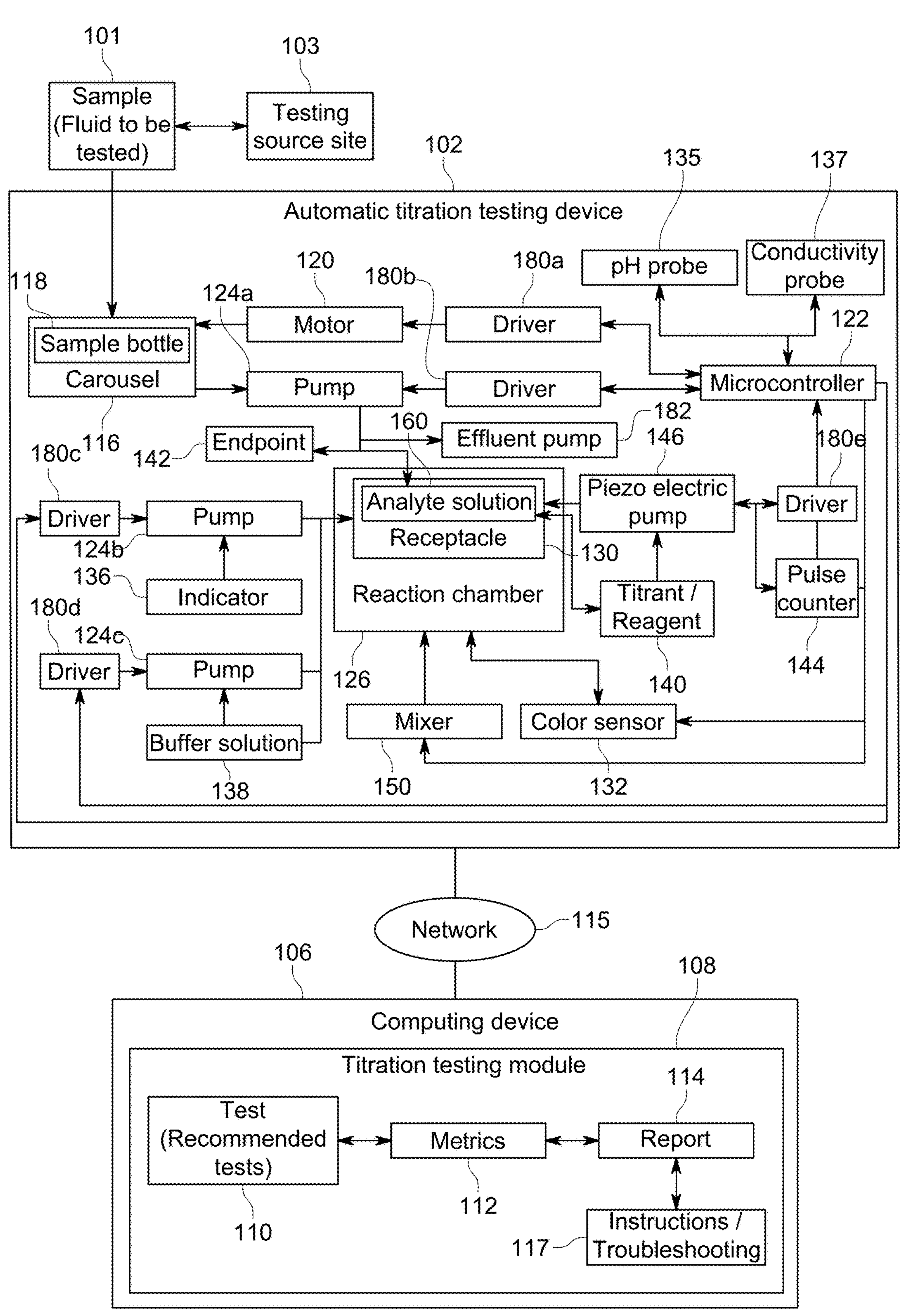
FIG. 1 is a block diagram of exemplary components of an automatic titration testing device and titration testing module on a computing device.

Many industrial facilities, food manufacturers, hospitals, semi-conductor manufacturers, data centers, and other types of facilities all use significant amounts of water for heating, cooling, and processing products, along with various other uses. However, the water in these systems can wreak havoc on equipment if not properly maintained. Water is naturally corrosive, particularly when in contact with metal, which can prematurely destroy expensive equipment. Water also naturally carries numerous minerals which can come out of solution and build up, termed “mineral scale”, on equipment causing flow restrictions and loss of heat transfer. Defending against these issues are of the utmost importance to industrial facilities because replacing equipment is oftentimes millions of dollars, and can even cause safety hazards.

The problems with corrosion and scale in these types of facilities is addressed by industrial water treatment professionals, who apply specialty chemicals and monitor water chemistry in a way that minimizes these problems from arising. Some of the most common types of systems that water treaters work with are steam boilers and the associated equipment, cooling towers, hydronic loops and process water that is used in numerous ways. Almost everywhere non-potable water is used in a facility a water treater should be helping to maintain it.

Measurement of the water chemistry is usually performed with a titration kit, either with burettes or a dropper test kit. In these test kits, most tests are colorimetric whereby the titration is performed until a color change is observed which allows one to calculate the concentration of the target analyte. By measuring different components in the water, a water treater can determine whether or not the conditions within the system are being properly controlled, or if adjustments need to be made in order to return to optimal operating conditions. Some examples of common chemical parameters that are checked include Chlorides, total hardness, Calcium Hardness, Sulfite, Phosphate, Phosphonate, Alkalinity, and many more metrics as further listed below.

To further complicate matters, many of these industrial water systems are comprised of numerous components. For this reason, it is often necessary to test not only the steam boiler but other components such as; water softeners, Deaerators, Boilers, Condensate receivers, surge tanks, and condensate polishers. By testing all these components, a water treater is often able to locate malfunctioning pieces of equipment throughout the system so that the issues can be addressed. The large number of components that make up many systems often means that numerous samples need testing. It is not uncommon to have upwards of 10 samples, each with up to several different analytes that are titrated. This can mean that for any given facility a water treater may need to perform upwards of 50 tests and interpret the data and trends for all of it, not an easy or straightforward task.

The inherently complicated nature of many industrial water systems means that most water treaters are highly educated and possess specialized knowledge. Couple this with the fact that proper water treatment can save a facility hundreds of thousands of dollars and one can surmise that the cost of such a professional is expensive. For this reason, most facilities try to minimize the number of visits by their water treatment professional and ask on-site staff to perform tests between visits by their contracted water treater. However, most often facilities staff have little to no knowledge of chemistry, which frequently leads to; confusion, bad data, or crucial tests not being performed. To compound the problem many facilities are operating with smaller and smaller maintenance crews, often leading to the chemical checks being skipped in favor of other tasks, which can cause problems to go unidentified for long periods of time.

Existing testing systems address only a minimal set of water chemistry and is only intended to be used on a single piece of equipment, mainly the boilers, while all other critical components and chemical analytes are left out. The prior art also does not offer data interpretation, an integral piece of the water treatment professional's duties. The prior art is meant to be an aid in controlling chemistry only and is not meant to fulfill the more comprehensive duties of a water treatment professional like performing a fully battery of tests, testing multiple pieces of equipment, trending data and providing suggestions/recommendations.

The present description is drawn to an automated liquid examination machine and system that uses titration, a user graphical user interface, and other components to provide data generation and interpretation of water samples. The titration device is able to test an array of industrially relevant water samples taken from a site, determine analyte concentrations and interpret data trends. The automatic titration testing machine may include a sample tray that holds N number of samples. The motile tray positions water samples for testing and moves them away after the selected titrations have been performed. Multiple reagents and titrants are stored in the device and can be independently pumped into a reaction chamber. A colorimeter and/or color sensor may be used to control the titration and reaction. The user is able to select pre-programmed and suggested tests to run for sampling the samples, or to create a custom set of titrations based on their unique needs.

The device may include a digital interface that can be operated wirelessly and that can store the tests and obtained data for each sample and sample set. One or more reports may be provided to the user with the obtained analyte concentrations that had been selected for each sample. The titration testing module is configured to execute one or more pre-programmed tests that initiate pre-programmed instructions for how much sample and buffer solution(s) is added during a titration process.

The automated titrating device is configured to be self-cleaning as well and has its own pumps to provide wash water and/or rinse water to clean a testing chamber. As noted, this machine will automate the titration process and in turn minimize human error when performing these tests. The automated titration testing device may be utilized to monitor and obtain data about water for industrial processes as well as for boilers, cooling towers, water heating loops, and/or swimming pools in one or more non-limiting embodiments. Additional details are provided with respect to the Figures.

FIG. 1 provides a block diagram of exemplary components of the automatic titration device 102 according to one or more non-limiting embodiments. The automatic titration testing device 102 may have a housing that holds multiple components shown in FIG. 1 for performing automated titrations. Titration is a technique to determine the concentration of a substance (analyte) by reacting it with a solution of known concentration (e.g. titrant 140 as shown in FIG. 1). This reaction typically involves gradually adding the titrant 140 from a burette or other conduit until the reaction reaches its completion point, known as the equivalence point, often indicated by a color change (e.g. endpoint 142 as shown in FIG. 1). In titration, the analyte is the substance whose concentration or quantity is being determined. It is the unknown solution that reacts with a known solution called the titrant. Titration uses a standard solution (the titrant 140 as shown in FIG. 1) of known concentration to react with the analyte solution (e.g. analyte solution 160 as shown in FIG. 1) allowing for the calculation of the analyte's concentration.

One or more components may be fully contained within the housing of the titration testing device 102. Alternatively, some components may be separately coupled to and in fluid communication or signal communication with the housing and other internal components of the titration testing device 102. The titration testing device 102 may be a single device or machine that contains multiple components, including the components shown in FIG. 1. The computing device 106 may be a separate computing device 115 in one or more non-limiting embodiments. In another embodiment, the computing device 115 may also be integrated into the automatic titration testing device 102.

Figure 9:
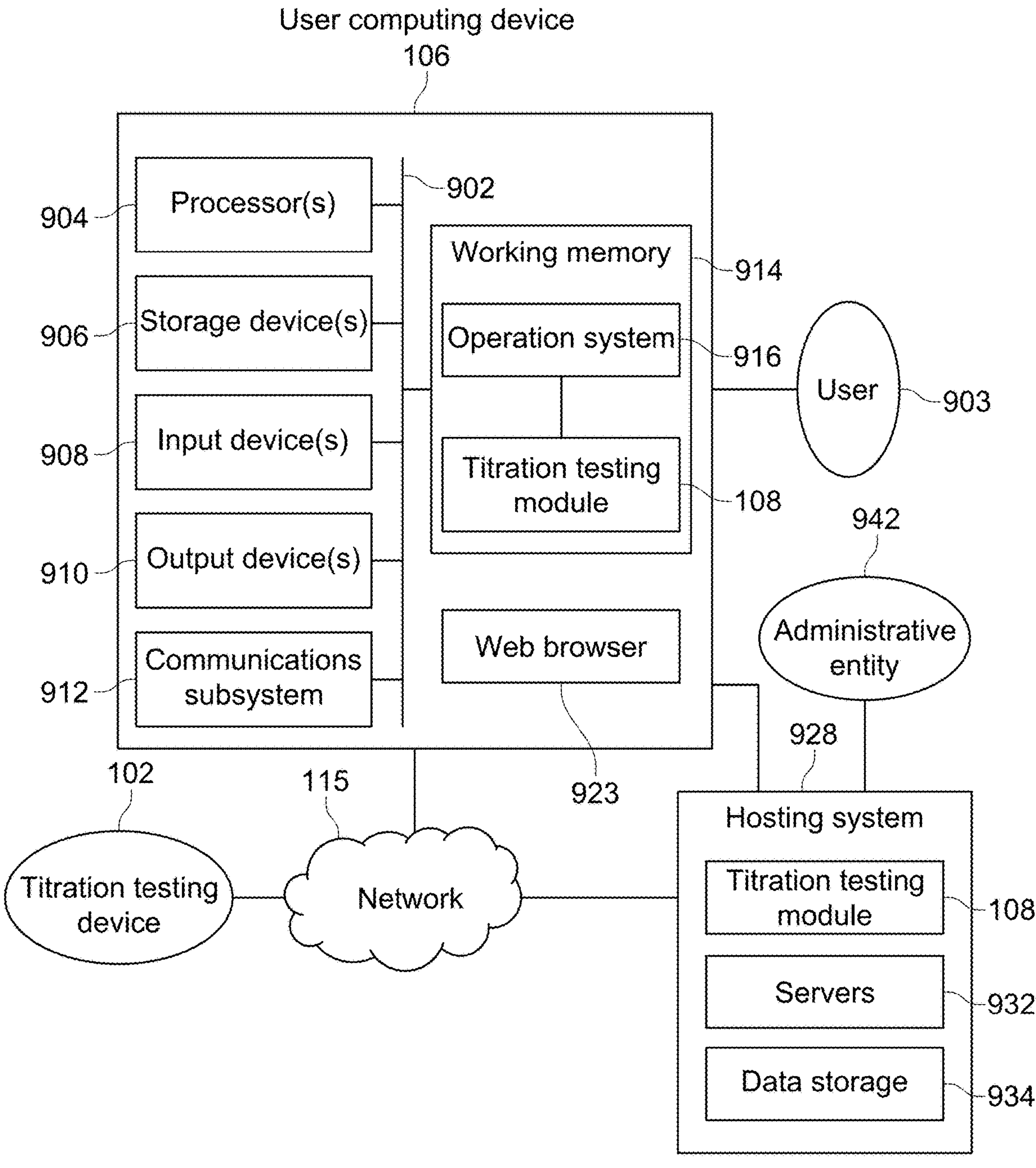
FIG. 9 is an exemplary block diagram with exemplary components for the computing device and system as described herein in one or more non-limiting embodiments.

In a non-limiting embodiment, the titration testing device 102 is coupled to a computing device 106. The computing device 106 may be any type of computer including but not limited to laptops or desktops. The computing device 106 may have its own processors and memory and input/output devices. Such components are also shown in FIG. 9 which details components of a computing device 106. As well, the computing device 106 may include a graphical user interface (e.g. output device 910 as shown in FIG. 9) for displaying information contained in a computer program/module (e.g. titration testing module 108) related to the titration testing to be performed in an automated manner on collected samples 101. Data and instructions may be communicated from the computing device 106 and the titration testing module 108 to the titration testing device 102 and/or microcontroller 122 of the titration testing device 102 over a network 115. Such networks 115 may include, but are not limited to, wireless networks, wired networks, BLUETOOTH, or any other type of signal communication network. The computing device 106 may be connected to the titration testing device 102 via wires and/or wirelessly in one or more non-limiting embodiments.

Advantageously, the titration testing module 108 may be programmed to include a plurality of predetermined tests or categories of tests 110 that may be of particular relevance when testing or analyzing fluid samples 101. Such tests 110 may be pre-labeled and may be presented to the user on a graphical user interface of the computing device 106. This may be in the form of a drop-down menu 600 (e.g. as shown in FIG. 6) in one or more non-limiting embodiments. The pre-programmed and selectable tests 110 may have or suggest a set of pre-determined relevant metrics 112 for which the titration testing device 102 is configured to automatically test. For example, the pre-programmed test 110*a* that is labeled "City Water" in FIG. 5 may include one or more metrics 112 that include, but are not limited to, testing the conductivity (e.g. metric 112*a* in FIG. 5), pH (e.g. metric 112*b*), M-alkalinity (e.g. metric 112*c*), Chloride level (e.g. metric 112*d*), and/or total hardness (e.g. metric 112*e*) of a fluid sample 101 obtained from a testing site 103. It is assumed that the user may want these 5 metrics, for example metrics 11*a*-112*e*, to be tested using accurate and automatic titrations testing using the titration testing device 102 for this particular type of test (e.g. city water test 110*a*). There may be a guide included with the titration testing module 108 that provides the user with an explanation of which metrics 112 are testable within each pre-established test 110.

In a non-limiting embodiment, the user can select all the pre-programmed metrics 112 included with the listed tests 110 or can select only the metrics 112 of interest to the user at the time. It is also noted that the user is not obligated to select a schedulable, listed test 110, but rather may choose to customize and create his or her own test 110 and set of metrics 112 that may not be already categorized in an available test category 110.

One of the intended goals of the titration testing module 108 is to obtain the readings and calculations for the metrics 112 and provide these readings and calculations after the titrations are performed by the automatic titration testing device 102 in the form of one or more visible tables 700 and/or reports 114. An exemplary table is shown in FIG. 7 showing how a set of readings and calculations may be displayed for each metric 112 that is tested for a particular test 110 and displayed in rows 702 and columns 704 of the table 700.

In a non-limiting embodiment, the titration testing module 108 further displays in such reports 114 or tables 700 whether the metric 112 being tested is in range or not in range. Accordingly, the titration testing module 108 may be pre-programmed to determine a desirable range for each metric 112 and to visually indicate to the user when the metric 112 is not within desired range or is in range. This is advantageous because it reduces the amount of decision making and research the user or technician has to undertake after receiving the data values and data shown in table 700 for example after a titration test has been performed for the one or more metrics 112. The titration testing module 108 may incorporate machine learning that allows the titration testing module 108 to be modified using supervised or semi-supervised learning or training. The titration testing module 108 is trained against a correct data set to identify a correct range and output for each metric 112.

The predetermined tests 110 may include a plurality of relevant metrics 112 for which a user may want to test one or more samples 101. For example, the metrics 112 may relate to one or more levels or readings obtained by performing titration tests on the sample water or fluid 101 for metrics that include, but are not limited to, conductivity, corrected conductivity, pH level, nitrite level, chloride level, total hardness, sulfite level, phosphate level, phoshonate level. A metric 112 may further comprise alkalinity level, which may further be broken down into p-alkalinity, m-alkalinity, and OH-alkalinity. As noted, additional metrics 112 may be tested other than those listed above. Each of these metrics 112 may be obtained using a titration with a known volume of fluid obtained from one or more samples 101 taken from a testing source site 103. As noted above, typically a human has to perform a manual titration on each sample and then calculate the values or levels associated with a particular metric 112 in order to ensure that the fluid stored at the source site 103 is in compliance with recommended values and ranges or required values and ranges by regulatory authorities for the relevant metrics 112. The readings and data values 706 obtained by the titrations performed by the titration testing device 102 and shared on the interfaces of the titration testing module 108 may be very valuable to help users, companies, and the like ensure that the fluid stored at the testing source site 101 is not lacking any chemicals or other items, and the titration testing module 108 may help determine if any corrective measures need to be taken if the readings taken from the samples with respect to a particular metric 132 show that there are any issues with the fluid at the testing source site 101. For example, the titration testing module 108 may provide concrete troubleshooting instructions and recommended best practices or procedures 114 for addressing if a metric 112 is found to be outside of a recommended range or level after a titration test is performed using the titration testing device 102 on a particular sample 101 obtained from the fluid testing source site 103.

The testing source site 103 may be any location with fluid and/or water samples that may need continuous testing via titrations. Such locations may include but are not limited to, industrial facilities such as industrial and water treatment facilities, food manufacturers, hospitals, semi-conductor manufacturers, data centers, hospitals, manufacturing facilities, and many other types of sites and facilities that utilize and/or process water regularly to accomplish a specific task or service.

It is noted that in some cases the titration testing device 102 is a standalone unit or device separate from the water source test site 103. The user may obtain the sample fluid 101 from the test site 103 and manually pour the samples 101 into the sample bottles 118 held on the carousel 116 for automated titration testing to occur. In alternative embodiments, one or more towers, boilers, coolers, holding units or other specific areas or devices within the source testing site 103 may be configured to incorporate the automated testing device 102 such that regular testing may be performed along with the normal function and operation of the towers, boilers, coolers, etc. While technicians are usually in the habit of manually collecting samples 101, as further elaborated upon below and separately conducting titration tests, it is envisioned that in one or more non-limiting embodiment, one or more fluid containers or units at a testing site 103 can be in direct fluid communication with the titration testing device 102 and its components for another method of delivery of the sample fluid 101 to the titration testing device 102 to occur.

A user may collect and obtain samples 101 from the testing site 103. The samples 101 may be one or more volumes or amount of fluid stored in one or more sample bottles/containers 118 that are specifically designed for or intended for use with a carousel 116. The fluid sample 101 from the testing site 103 may be manually poured or transferred into the cavities 206 of the one or more sample containers 118 that are specially configured to fit into container holders or openings of the carousel 116 (e.g. as shown in FIG. 2 in a non-limiting embodiment).

Figure 2:
FIG. 2 is a pictorial illustration of a sample carousel and sample bottle that is part of the automatic titration testing device.

The carousel 116 is intended to be a mobile tray with openings, such as, but not limited to, openings 202 as shown in an exemplary illustration in FIG. 2, to hold bottles 118 designed to fit in the carousel openings 202. The carousel 116 is configured to move or rotate in a circular manner so that different sample bottles 118 housed or stored in the openings 202 of the carousel 116 can be accessed by one or more pumps 124 integrated with the titration testing device 102 to pump out of the sample bottles 118 a predetermined amount of sample fluid or water for further testing via titration. The titration testing module 108 will know how many sample bottles 118 are in the carousel 116 based on the user input. The sample bottles 118 in the carousel 116 will be labeled (1, 2, 3, etc.) and on the GUI (graphic user interface) of the titration testing module 108, the user can select the sample type, and tests, for each sample bottle 118 that matches its position in the carousel 116. Any entries that are left blank will be omitted from that round of testing.

Multiple pumps are utilized throughout the process including pump 124*a*, 124*b*, 124*c*. 124*d*. and additional pumps not shown on the block diagram to pump fluid from one location to another in and out and around the titration testing device 102.

It is noted that the carousel 116 may be integrated within or inside of a housing of the titration testing device 102 in one embodiment. In another embodiment, the carousel 116 may be located outside of the housing of the titration testing device 102 and still be in fluid communication with the reaction chamber 126 and reaction chamber receptacle 130 in particular where the fluid water from the sample bottle 118 is directed while undergoing testing via titrations within the titration testing device 102. In a non-limiting embodiment, the reaction chamber receptacle 130 may be clear to ensure easy reading of color changes within the reaction chamber receptacle 130 during the titration process by the color sensor 132.

As noted in FIG. 1 and in FIG. 2, the titration testing device 102 may include and/or be coupled to and be in signal communication with a motor 120 that is operated by a microcontroller 122 that is stored within or associated with the titration testing device 120. The titration testing device 102 may have its own power source and may be activated on or off as desired by the user.

The motor 120 may be a stepper type motor in one or more non-limiting embodiments, although, other types of motors may alternatively be used. As known in the art, the microcontroller 122 may be a self-contained computer that is contained on an integrated circuit (IC). The microcontroller 122 typically includes a central processing unit (CPU), memory (e.g. RAM and ROM), I/O peripherals (timers, counters, ADCs, etc.) on a single chip. The microcontroller 122 may perform a number of tasks for the titration testing device 102 in conjunction with the titration testing software module 108 stored on the computing device 106. The microcontroller 122 may process instructions from the titration testing software module 108 to commence titrations based on a series of selected tests 110 to determine one or more metrics 112 present in the samples 101 needed testing. The microcontroller 122 may further provide instructions to the various pumps 124, 146 and probes 134 as well as to the color sensor 132, pulse counter 144, and other components associated with the titration testing device 102 to start or stop one or more functions of the titration testing process.

A number of drivers, such as drivers 180*a*, 180*b*, 180*c*, 180*d*, and 180*e* may be used throughout the process that enables the titration testing module 108 to communicate with one or more components of the titration testing device 102. Alternatively, the drivers 180*a*-180*e* may also communicate with the motor 120 and/or microcontroller 122. There may be additional drivers 180 not shown in FIG. 1 that also are used to communicate with one or more components of the titration testing device 102.

Driver 180*a* may be used to communicate operating instructions with motor 120 to communicate instructions from the titration testing module 108 (e.g. operating system) and/or the microcontroller 122. Driver 180*b* may be used to communicate operating instructions from the microcontroller 122 and/or titration testing module 108 to pump 124*a* which in turn is configured to pump solution from a sample bottle 118 on the carousel 116 to the reaction chamber receptacle 130 which will become the analyte solution 160 as titrant 140, indicator 136, and other chemical elements and/or buffer solution 138 may be added selectively by the titration testing device 102 (e.g. upon instruction from the titration testing module 108 and/or microcontroller 122).

The driver 180*c* may be used to pump via pump 124*b* indicator dye 136 to the reaction chamber receptacle 130 in alignment with the previous remarks. The driver 180*d* may be used to convey operating instructions to pump 124*c* which pumps buffer solution 138 to the reaction chamber receptacle 130. The driver 180*e* may be used to convey operating instructions to the piezo electric pump 1466 and/or pulse counter 144 from the microcontroller 122. As noted, it the titration testing device 102 may include multiple additional drivers 180 to convey operating instructions for one or more components contained in and/or associated with the titration testing device 102. Additionally, there may be additional pumps 124 other than those shown in FIG. 1 that are used to pump in or out one or more fluids to components of the titration testing device 102

Figure 3:
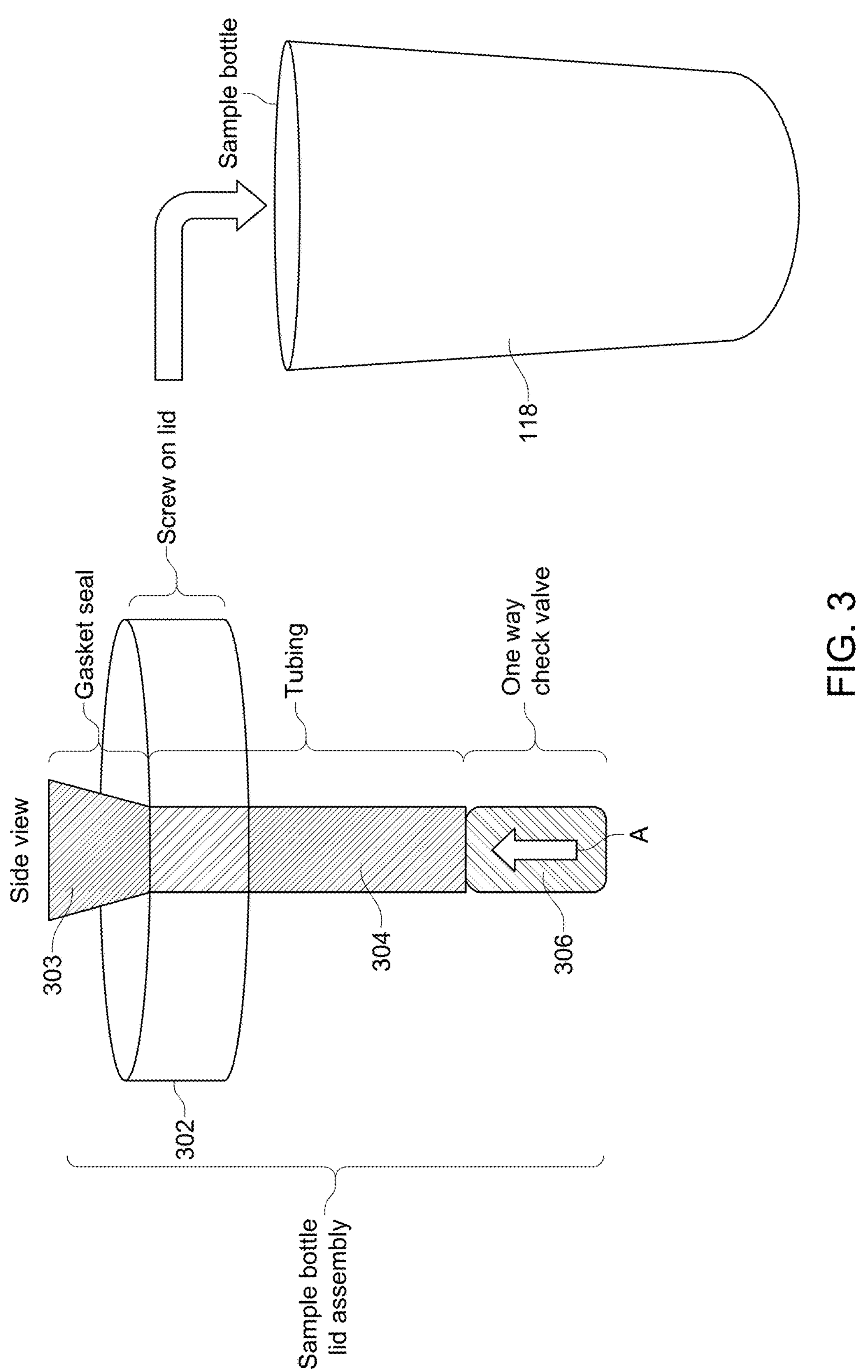
FIG. 3 is a pictorial illustration of an airtight sealing lid assembly that is controllable by the automatic titration testing device to be fitted over a sample bottle that is being tested.
Figure 4:
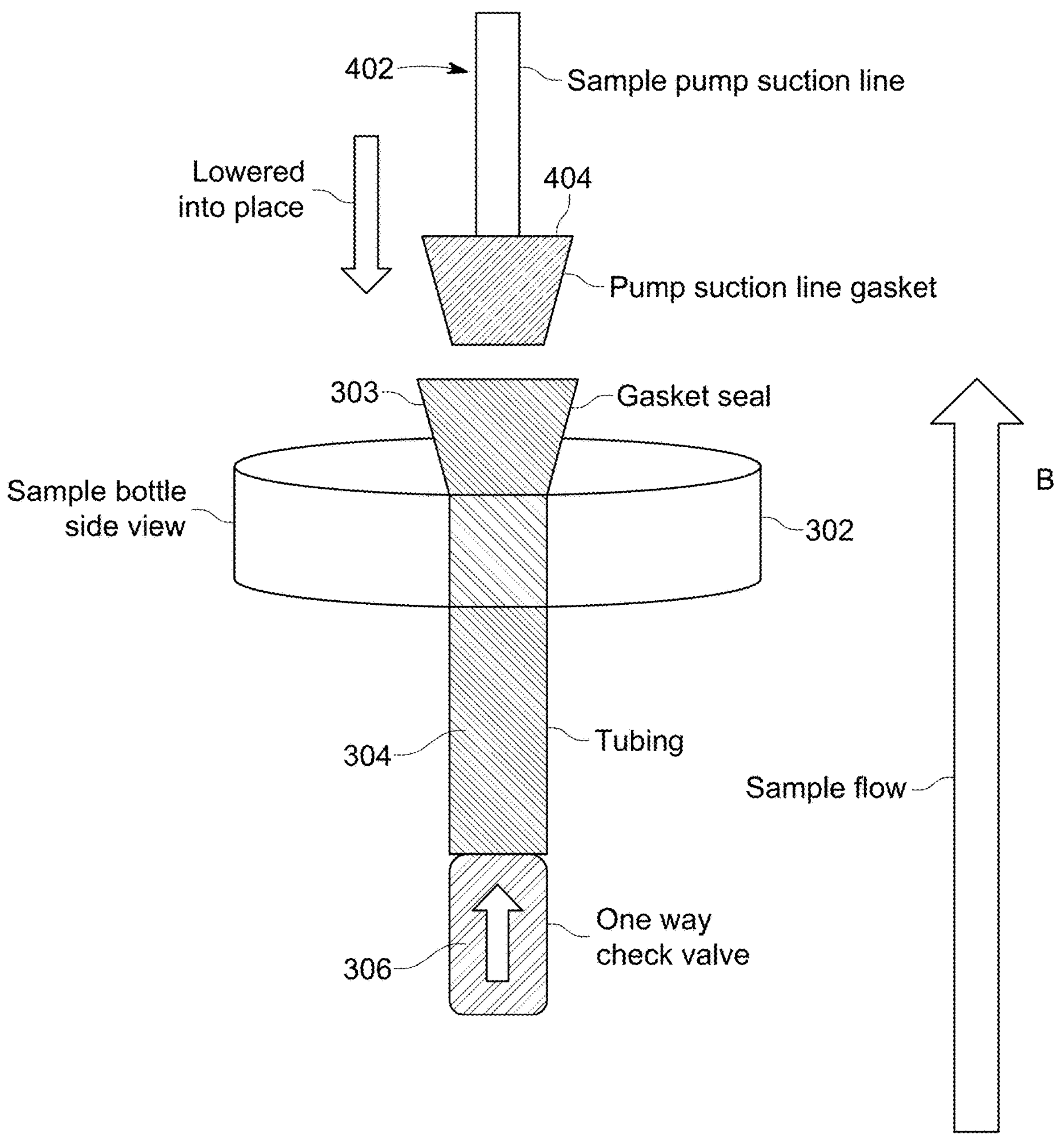
FIG. 4 is a pictorial illustration of an airtight system for applying the lid on a sample bottle to be tested on the sample carousel of the automatic titration testing device.

The motor 120 may be used to rotate the carousel 116 as needed to turn the carousel 116 and to position the desired sample bottle 118 as stored within one of the particular sample bottle openings 202 (e.g. as shown in FIG. 2) beneath an intake suction line (e.g. 402) associated with or integrated with the titration testing device 102 to pump the sample fluid 101 held within the sample bottle 118 needing testing into the reaction chamber receptacle 130. There may be a driver 180 that communicates instructions from the microcontroller 122 to the motor 120 which can then control the carousel 116 to rotate the carousel 116 into position. In particular, to rotate the carousel 116 to provide access to a specific spot or location in the carousel 116 that houses or holds a particular sample bottle 118, which can then couple for example, with the lid assembly 300 and components as shown in FIGS. 3-4 in a non-limiting embodiment.

Notably, the system 100 for the titration testing device 102 includes an airtight sealing system that can be used to ensure that sample fluid 101 sucked into or pumped into the reaction chamber receptacle 130 that is stored or housed within the reaction chamber 126 of the titration testing device 102 is done in an airtight manner that minimizes any oxygen being added to the sample fluid 101 as the sample fluid 101 is pumped into the titration testing device 102 and into the reaction chamber receptacle 130. This may be due to the design and structure of the sample bottle lid assembly 300 as shown in a non-limiting embodiment in FIG. 3. In a non-limiting embodiment, as shown in FIG. 3, the titration testing device 102 may be coupled to or integrate an airtight lid 302 configured to screw on or otherwise be tightly placed onto a particular sample bottle 118 while the sample bottle 118 is stored or held in place on the carousel 116. The lid 302 may have a gasket seal 302 generally centrally positioned or attached to a top surface of the lid 302. Tubing 304 may descend from an interior hole that aligns with a hole of the lid 302 and the gasket seal 302. There may also be a one way check valve 306 attached to a lower end or integrated into a lower end of the tubing 304. The tubing 304 with the check valve 306 is designed to be lowered onto a sample bottle 118 with sample fluid 101 retained or held inside of the sample bottle 118 that is about to undergo titration testing for determining readings and data values 706 for one or more metrics 112 of the fluid sample 101. FIG. 4 shows an exemplary pump suction line 402 that includes an airtight nozzle 404 or other fluid conduit unit at the end of the pump suction line 402. The pump suction line may already be attached to the gasket seal 303 of the lid assembly 300 prior to lowering the lid assembly 300 down onto the top surface 205 of the sample bottle 118. In other embodiments, a user may attach the entire lid assembly 300 to the nozzle 404 such that the nozzle 404 fits within the gasket seal 303 of the lid assembly 300. The gasket seal 303 may be in tight fluid communication with the lid 302 and the tubing 304 and the one way check valve 306, and every piece may be tightly fitted together, including with adhesives or fasteners, to prevent any loosening or slipping of any parts from each other for the lid assembly 300. The lid 302 is intended to fit onto the top surface 205 of the sample bottle 118, such that the tubing is inserted into the cavity 206 of the sample bottle 118. The pump suction line 402 is connected to a pump 124 associated with or integrated with the titration testing device 102, such that, when the titration testing device 102 is activated, the pump 124 is able to pump the sample fluid 101 from the sample bottle 118 in an airtight manner to the receptacle 130 stored in the reaction chamber 126 in one upward direction as shown by the arrow B. The sample fluid 101 is intended to flow upwards in the direction of arrow B into the sample pump suction line 402 upon activation and request for titration testing to begin. Using such an airtight system will ensure more accurate test results of the samples 101.

The reaction chamber 126 is an important unit within the titration testing device 102, because the reaction chamber 126 houses the reaction chamber receptacle 130. The reaction chamber receptacle 130 is the receptacle where a known, pre-determined volume of the fluid sample 101 is pumped and then mixed with one or more important elements of the titration process, which becomes the analyte solution 160. In a non-limiting embodiment, the reaction chamber receptacle may be a flask or container. It may also be preferable for the receptacle to be transparent, in particular so that the color sensor 132 is enabled to sense when an endpoint 142 occurs i.e. a color change.

The fluid sample 101 may be mixed with an indicator solution 136 and/or titrant (also known as reagent) 140 to undergo titration testing. The goal of the addition of the titrant 140 is to reach an endpoint 142. The term "indicator" as used herein may interchangeably be used with the term "injector dye" and/or "indicator dye." The endpoint 142 in titration is known as the point where the color of the testing fluid held within the reaction chamber receptacle 130 (to which has been added indicator 136 and titrant 140) undergoes a color change after a sufficient amount of titrant 140 is added. In some cases, depending on the metric 112 being tested, buffer solution 138 is also added to the sample fluid 101 pumped into the reaction chamber receptacle 130. Buffer solutions 138 may be added to titration reactions occurring within the reaction chamber receptacle 130, especially in complexometric titrations like EDTA titrations, to maintain a stable pH and ensure the proper reaction conditions for the titration to occur accurately. This is crucial for reactions where pH affects the binding or reactivity of the titrant 140.

It is noted that the titration testing device 102 may include one or more containers for multiple different types of titrant 140. The appropriate container or receptacle of titrant 140 that is used to pump the appropriate or desired titrant 140 to the reaction chamber receptacle 130 for performing a titration depends upon which sample test type 110 and metric 112 was selected by the user. For example, one type of titrant 140 is pulled from a container when testing for alkalinity as a desired metric 112 in a sample 101 and another type of titrant 140 is pulled from another container when testing for chloride levels as a desired metric 112. Accordingly, different metrics 112 require use of different titrants 140 and will dictate what type of titrant 140 the testing device 102 uses for a specific titration. Accordingly, a plurality of bottles or containers to hold a variety of types of titrants 140 are also either stored within the titration testing device 102 or at least may be stored outside of the titration testing device 102, but are pumpable by one or more pumps and conduits and are in fluid communication with the analyte solution 160 and the reaction chamber receptacle 130 where the testing occurs in the reaction chamber 126. There are a number of different titrants and indicators that are used. Each test 110 and metric 112 has unique combinations of both titrants 140 and indicators 136 that the titration testing device 102 is programmed to recognize how much to add and which titrants 140 and indicators 136 to add to an analyte solution 160 to perform testing.

The indicator 136, the buffer solution 138, and the titrant 140 may be contained within containers that are integrated into or at least in fluid communication with the reaction chamber 126 and the reaction chamber receptacle 130. A series of conduits may be connected to such containers for the indicator 136, buffer solution 138, and/or titrant 140 in a manner to ensure that the indicator 136, buffer solution 138, and/or titrant 140 can be pumped into or caused to flow from their respective containers into the reaction chamber 126 and reaction chamber receptacle 130 in an automated manner upon receiving a command or signal to proceed from the microcontroller of the titration testing device 102 and/or the titration testing module 108.

The titration testing device 102 may further comprise a mixer 150. A mixer 150 is a device that causes the fluid sample 101 stored within the reaction chamber receptacle 130 to be mixed with any other fluids added to the fluid sample 101 in the reaction chamber receptacle 130, such as, but not limited to, indicator 136, buffer solution 138, titrant 140, and/or other fluids. The mixer 150 may help to ensure that the fluid sample 101 is homogenously mixed with the indicator dye 136, buffer solution 138 if applicable, and/or titrant 140. The mixer 150 ensures mixing occurs as needed with the analyte solution 160 held in the reaction chamber receptacle 130 and the reaction chamber 126.

A color sensor 132 may be coupled to the reaction chamber and the reaction chamber receptacle 130. The color sensor 132 may be angled to see and sense when a color change occurs during the titration testing process as the titration test is run in the reaction chamber receptacle 130. The color sensor 132 may be positioned very closely to the reaction chamber receptacle 130 so as to sense that a color change has occurred. Once the color sensor 132 provides the indication that the color change has occurred, this is a signal for the titrant 140 to stop being added to the reaction chamber receptacle 130. Accordingly, the endpoint 142 has been reached whereby the color change occurs and calculations may be performed to determine a reading or obtain a data value for a particular metric 112 of interest to the user with respect to the fluid sample 101 being tested. The microcontroller 122 may be in electrical communication with the color sensor 132 and with the titrant 140 to facilitate the process of stopping the pumping of the titrant 140 into the reaction chamber receptacle 130.

It is noted that the color sensor 132 and color change process associated with the titration testing device 102 is desirable because the system 100 only has to determine when the color change occurs and can conclude that the titration has concluded. The system does not have to look for a gradient or the like as some other titration testing processes use. This system is more feasible for the color sensor 132 and provides more accurate results.

The titration testing device 102 may further comprise a pulse counter 144. A pulse counter 144 refers to a counter that is used to count the number of drops of titrant 140 added to the reaction chamber receptacle 130 during the titration testing process. In a non-limiting embodiment, the microcontroller 122 is configured to act as a pulse counter 144 and is based on the number of electric pulses sent to the piezo electric pump 146 from a pump driver (e.g pump driver 180) which essentially counts the number of times a diaphragm in the titration testing device 102 is actuated. Since the diaphragm is a known and constant volume, the number of pulses is multiplied by the volume of the diaphragm/pump chamber to obtain the volume of the titrant 140 before reaching the endpoint 142 (where the color changes).

In a non-limiting embodiment, the pulse counter 144 may be a drop counter that is a specialized type of pulse counter design to count individual drops of titrant 140 as the drops fall from a burette or the like into the analyte solution 160 stored in the reaction chamber receptacle 130. The pulse counter 144 may operate in conjunction with an optical or infrared sensor (and/or the color sensor 132) to detect each drop of titrant 140 as the drop passes through a small window or sensing area. A pulse is generated for each detected drop of titrant 140, and the pulse counter 144 increments its count. The pulses can be converted to volume for purposes of making calculations and obtaining data related to the tests 110 and the metrics 112 for analysis purposes of the fluid samples 101.

In order to determine the precise volume of titrant 140 added, the pulse counter 144 has to be calibrated to determine the average volume of each drop. By multiplying the total number of counted drops by the average drop volume, the system 100 accurately calculates the volume of titrant 140 added. It is noted that the pulse counter 144 can be integrated with other sensors, such as pH sensors or conductivity probes 137 included in the titration testing device 102. This may enable a titration curve to automatically be generated and displayed on the titration testing module 108, which allows for a more automated and precise determination of the equivalence point. The automated process of determining when the color change/endpoint 142 occurs helps to free up the user or technician's time for other tasks and also the system 100 provides more consistent and accurate results via the titration testing process.

The titration testing device 102 may further comprise or include a piezoelectric pump 146, which is a specialized pump that utilizes the piezoelectric effect to move fluids. The piezoelectric pump 146 applies an electrical signal to a piezoelectric element, which then mechanically deforms, driving a diaphragm or valve to pump the fluid. Such pumps 146 are known for their ability to handle small volumes of fluid with high precision. The piezoelectric pump 146 may be use to precisely deliver the titrant 140 accurately and in an automated manner for the automated titration testing device 102.

The titration testing device 102 may further comprise one or more pH probes 135 and/or conductivity probes 137. A pH probe 135 is also known as a pH electrode or pH sensor that can be used to measure the acidity or alkalinity of the analyte solution 160 held in the reaction chamber receptacle 130 by measuring its pH level. The pH scale ranges from 0 to 14, with 0 being the most acidic, 7 being neutral, and 14 being the most alkaline. Similarly, the conductivity probe 137 may be a device used to measure the electrical conductivity of the analyte solution 160 held in the reaction chamber receptacle 130. The conductivity probe 137 may be a sensor or EC probe.

In a non-limiting embodiment, the pH probe 135 and the conductivity probe 137 are self-calibrating. The system 100 may be configured to have the pH probe 135 and the conductivity probe 137 self-calibrate prior to every titration testing or may be programmed for another period of time. This will help to ensure more accurate testing and data can be obtained from the titration testing process, as usually, these probes, if not self-calibrating, will drift over time and the accuracy of the data analysis is reduced. Further, information may be provided about the method of using the titration testing device 102 and the titration testing module 108 and the data results with respect to FIGS. 5-9.

Self-calibrating the pH probe 135 and the conductivity probe 137 may occur by using standard pH and conductivity solutions that will be pumped into the reaction chamber 126 and held values in the microcontroller 122 are adjusted to match the standard solutions. Generally, this is done with pH 4, 7, and 10 solutions for pH and conductivity solutions ranging from 100 micromhos up to 5000 micromhos.

Notably, microcontroller 122 of the titration testing device 102 includes pre-programmed instructions for when to add sample water, titrant 140, buffer solution 138, indicator dye 136, and any other elements required during the titration testing process. The microcontroller 122 of the titration testing device 102 operates in conjunction with the pH probe 135, conductivity probe 137, mixer 150, pulse counter 144, and piezoelectric pump, sample pump, and effluent pump 146 during the various titration testing processes.

The order of the testing of the metrics 112 may be determined by following an order as executed and instructed from the selected test 110 via the titration testing module 108. In a non-limiting embodiment, the execution of the test 110 is performed first on all analyte solutions 160 for any given sample set before moving onto another sample set contained on the carousel 116. Only after the execution of testing of all metrics 112 for a sample set 101 is performed should code for another set of tests on the next sample 110 be performed.

It is noted that the titration testing device 102 is intended to be self-cleaning. Accordingly, the reaction chamber receptacle 130 is cleaned after each titration test is concluded. Upon concluding a titration, the analyte solution 160 may be pumped out or ejected out from the reaction chamber receptacle 130 using one or more effluent pumps 182 designed to remove the waste solution after testing is completed, whereby the reaction chamber receptacle 130 is configured to be cleaned so that another sample 101 may be pumped into the reaction chamber receptacle 130 and further testing occurred if needed. Next, a volume of wash water/rinse water 128 may be pumped/injected into the reaction chamber receptacle 130 upon conclusion of testing. The mixer 150 may be employed or activated to assist in mixing and cleaning out the reaction chamber receptacle 130 in order to ensure that the remnants of the analyte solution 160 from a prior titration test are no longer remaining in the reaction chamber receptacle 130 to ensure more accurate results for a subsequent titration testing.

Figure 5:
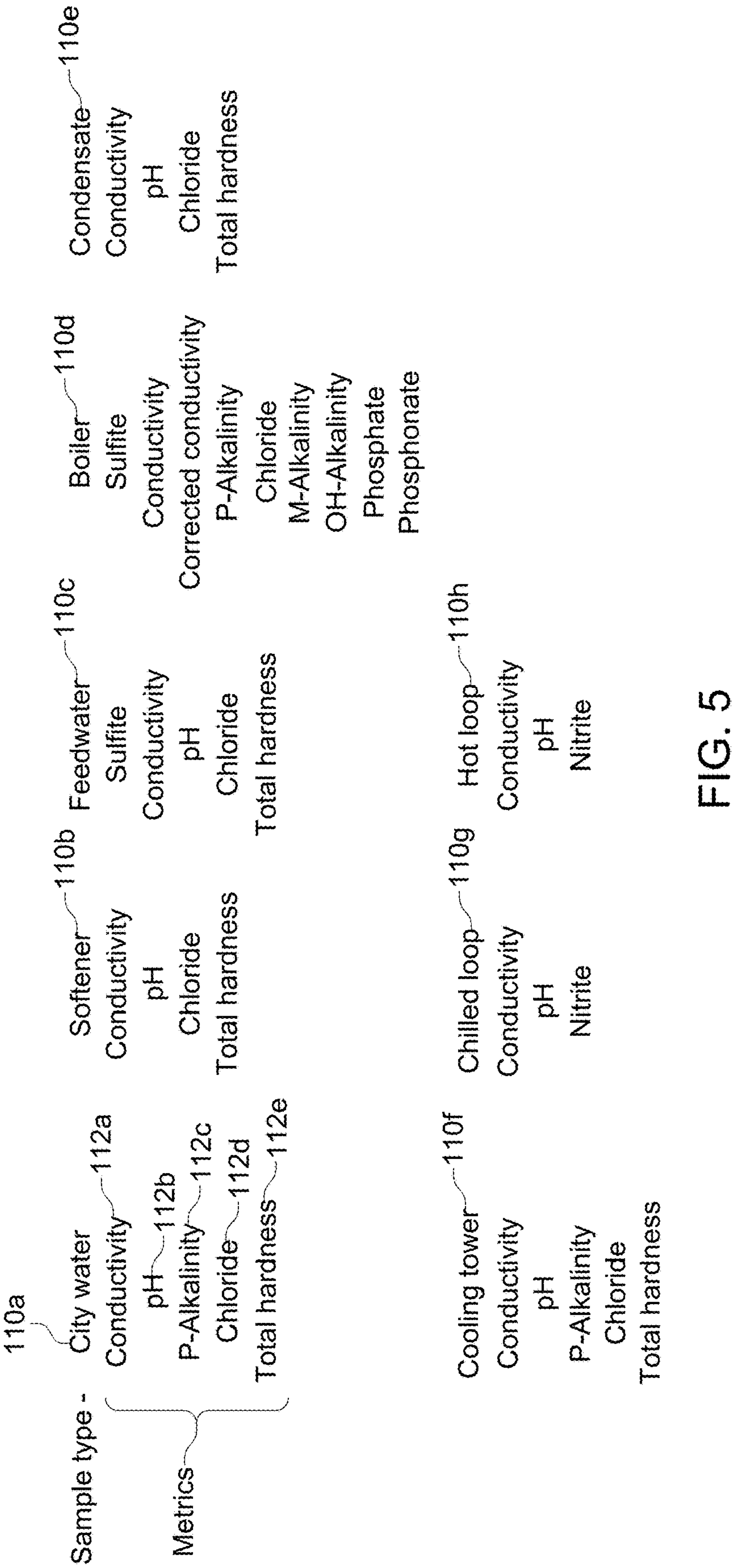
FIG. 5 is a pictorial illustration of exemplary pre-programmed tests with a list of pre-determined metrics or analytes to be tested using the automatic titration testing device.
Figure 6:
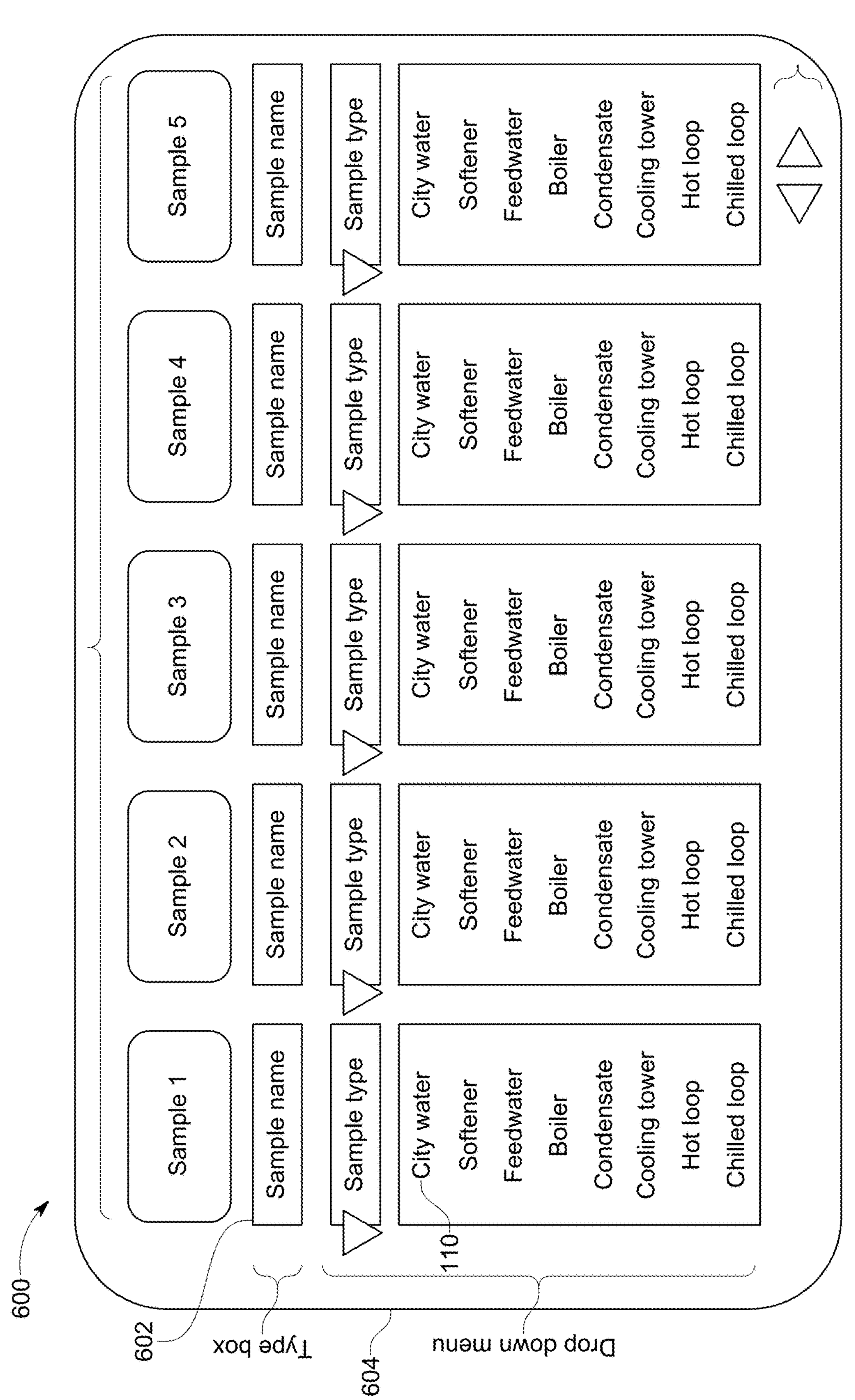
FIG. 6 is a pictorial illustration of a screenshot from the titration testing module with exemplary pre-programmed or selectable tests with metrics of interest for samples being tested by the titration testing device.

Turning to FIG. 5, FIG. 5 shows an exemplary set of pre-programmed tests 110 that may be useful, in particular, to incorporate into the titration testing module 108 as pre-programmed, selectable options to a user/technician. It is noted that these types of tests 110 may be particularly useful for industrial water operations and wastewater or municipal water sites 103. FIG. 5 is intended to demonstrate that these tests 110 may be set up to best suit the types of titration tests and metrics sought to be analyzed by a technician or user. However, the system 100 is not limited to the types of tests 110 with the same labels or categories as shown in FIG. 5. These labels and categories for the tests 110 are merely exemplary. FIG. 5 intends to show that the tests 110 may come with pre-selectable metrics 112 that the user may select all of or some of for automated titration testing and analysis of the data to occur by the titration testing device 102 and/or titration testing module 108. As noted above and as shown in FIG. 5, in a non-limiting embodiment, it may be useful to obtain metrics 112 related to the ranges or levels associated with conductivity, pH, –, chloride levels, calcium hardness, total hardness, sulfite levels, corrected conductivity, p-alkalinity, m-alkalinity, OH-alkalinity, phosphate, and phosphonate, as well as nitrite levels for the fluid samples 101 in one or more non-limiting embodiments. One or more formulas or calculations may be performed for providing such metrics 112 solely by using the known volume of the sample fluid 101 as pumped into the reaction chamber receptacle 130 along with the obtained, calculated volume of titrant 140 that is added to the sample fluid 101 (i.e. after it becomes the analyte solution 160).

The titration testing device 102 may test city water in a sample test type 110*a* which may appear on one or more interfaces of the titration testing module 108 for selection by a user. Another test type may be to test for water softeners and this may be offered as a sample test type 110*b* for example. Water softeners are common pieces of equipment for steam boiler and domestic water systems. They are designed to remove calcium and magnesium hardness from water. The titration testing device may also provide a feedwater sample test type 110*c*. The term feedwater refers to a tank, prior to a steam boiler system, where the water is preheated and commonly treated with chemistry prior to entering the boiler. This piece of equipment plays an important role in oxygen removal prior to water entering the boiler. Most often the water in this tank is comprised of both condensate and fresh makeup water from a water softener.

Another sample test type is shown in FIG. 5 as test type 110*d* for a boiler. Boilers are common pieces of industrial equipment designed to either produce steam or hot water to be used for heating, sterilizing, cooking, and various other processes. Another sample test type shown in FIG. 5 is for condensate 110*e*. As steam loses energy, in the form of heat, the gaseous water i.e. steam, is turned back into liquid form, which is termed condensate. Condensate generally is captured and returned to a feed tank if the use of the steam allows such action. Most often condensate is sent to remote condensate receivers where it is stored until the level in the tank is sufficient to initiate a pump to return it to the feedwater tank.

Another test type that may be offered to test one or more metrics 112 is for a cooling tower sample test type 110*f*. A cooling tower is a piece of equipment that is used to cool processes via direct or indirect contact with water. The term cooling tower is meant to include cooling towers, condensers, water cooled fluid coolers, air washers, evaporative condensers, and all other forms of the equipment used in cooling. Cooling towers are commonly paired with chillers, process heat exchangers, and ammonia refrigeration systems in indirect/non-contact cooling systems. Direct contact cooling is also possible and occurs when water is sprayed directly on products, such as plastic extrusions, where after cooling the product, the water is collected in a sump or basin and pumped back to the tower to be cooled and reused. Cooling towers function by evaporating a percentage of the water that is pumped over the fill media in the tower, effectively removing heat from the remaining water and cooling it.

Another test 110 offered as a pre-programmed option by the titration testing module 108 may be for the hot loop test 110*h*. Hot loops generally fall under the term "Hydronic loop". These are fully closed systems where water should not be lost or made up. Hot water is pumped around buildings to heat exchangers, most often for HVAC heating but can also be used for other purposes. The water here is generally heated by hot water boilers. Another test offered may be the chilled loop test type 110*g* which may apply for cooling. This may be commonly paired with cooling towers via a chiller to provide HVAC and process cooling.

It is intended that the microcontroller's 122 processing unit and/or the processing unit 904 of the computing device 108 may function to calculate and determine one or more metrics 112 upon determining that the endpoint 142 has been achieve during titration. This may include providing the known values obtained from the volumes associated with the sample fluid 101 as injected into the reaction chamber receptacle 130 and the obtainable, known volume of titrant 140 added to the analyte solution 160 and using these values to calculate one or more metrics 112.

For example, conductivity as a metric 112 may be determined by measuring the electrical conductivity of the analyte solution 160 as titrant 140 is added. This may be done using the conductivity probe 137, which measures the resistance of the solution 160 between two electrodes. The conductivity is then used to track the reaction and determine the equivalence point. The conductivity probe 137, which may be self-calibrating, may be immersed in the analyte solution 160 in the reaction chamber receptacle 130. An electrical current may be applied and the resistance of the solution is then measured. The conductivity is then calculated from the resistance. As the titrant 160 is added, the analyte solution's 160 conductivity changes due to changes in ion concentration and mobility. By plotting the conductivity readings against the volume of the titrant 140 added, a characteristic curve is obtained. The equivalence point is typically marked by a sharp change in the curve, indicating the completion of the reaction.

To obtain the pH metric 112, the system 100 and the titration testing device 100 may use a pH probe 135. The pH probe 135 continuously measures the pH of the analyte solution 160 as titrant 140 is added, creating a pH titration curve (which may be generated and displayed on the titration testing module 108 for each test 110 and/or metric 112 as tested). This curve helps determine the equivalence point, where the analyte 160 and titrant 140 have reacted stoichiometrically. The equivalence point is often indicated by a sharp change in pH on the curve. The pH probe 135 is inserted into the solution being titrated (the analyte solution 1660), and the 160 titrant is added slowly and accurately from a burette. The solution is mixed by the mixer 150 to ensure proper mixing. In order to measure the pH level of the analyte solution 160, the pH probe 135 continuously monitors the pH as the titrant 140 is added. In order to create the titration curve, the pH readings are plotted against the volume of titrant 140 added, creating a pH titration curve. The equivalence point is the point on the curve where the pH changes most dramatically. This point corresponds to the point where the moles of titrant 140 added are equal to the moles of analyte in the original solution. In order to determine the concentration, by measuring the volume of titrant 140 required to reach the equivalence point and knowing the concentration of the titrant 160, the concentration of the analyte solution 160 can be calculated.

In order to calculate or determine readings for alkalinity using titration, a standard acid solution is used, and the endpoint 142 is reached when the analyte solution's 160 pH level drops to a specific value (typically 8.3 or 4.5). The amount of acid needed to reach this endpoint 142 determines the analyte solution's 160 alkalinity. The titration steps when focusing on alkalinity as a metric 112 may include pumping a representative sample 101 from the sample bottle 118 in the carousel 116 to the reaction chamber receptacle 130 for testing. For acid titration, a standard acid solution (e.g., hydrochloric acid or sulfuric acid) may slowly be added to the sample 101 in the receptacle 130, while constantly stirring. The endpoint 142 has to be determined. This may be done using the indicator dye 136 and color sensor 132 and/or a separate pH probe 135, to monitor the change in pH as the acid is added. The endpoint 142 is reached when the pH reaches a predetermined value (e.g., 8.3 for p-alkalinity or 4.5 for m-alkalinity). Next, the system 100 may record the exact volume of acid used to reach the endpoint 142. A calculation may be performed where the volume of acid is used and the acid concentration to calculate the alkalinity, typically expressed as mg/L as calcium carbonate (mg/L $CaCO_3$). For this example, the titration testing module 108 may be programmed to determine the alkalinity of a sample 101 as tested by the titration testing device 102. The formula may, for example, ml titrant multiplied by the normality of titrant multiplied by the equivalent weight equals mg $CaCO_3$.

Each pulse from the piezoelectric pump 146 may be approximately 150 microliters of 0.2N titrant solution If, in a non-limiting example, 0.15 mL of titrant 140 is multiplied by 0.2N titrant and then multiplied by 50 (equivalent weight), the result of 15 mg alkalinity in the sample solution as $CaCO_3$ may be determined by the titration testing device 102 in combination with the microcontroller 122 and titration testing module 108. In this manner one can count the number of pulses sent to the piezo electric pump 146 until a color change is observed by the color sensor 132, indicating the titration is complete, and multiply the 15 mg alkalinity per drop to calculate the alkalinity of the sample solution 101.

For the titrations as performed by the titration testing device 102, each drop or added amount of titrant 140 is equal to some amount of analyte present in the analyte solution 160 based on a standard volume of the sample 101 present in the reaction chamber receptacle 130. As an example, with a 10 ml sample volume, the microcontroller 122 may cause 5 drops of indicator dye 136 to be added to the receptacle 130 and then add the appropriate titrant 140 depending on the metric 112 being tested for. Then the microcontroller 122 and/or a separate pulse counter 144 may count the number of drops of titrant 140. The drops or amount of titrant added 140 are monitored and counted until an endpoint 142 is reached. The number of drops added may be counted by 10 (e.g. the ppm from each drop) to get the final concentration in the sample 101 for a data/value related to the metric 112 being tested for.

In order to determine total hardness as a metric 112, the sample water 101 may be pumped from the sample bottle 118 in the carousel 116 to the reaction chamber receptacle 130. To determine total hardness, typically, in a non-limiting embodiment, EDTA (ethylenediaminetetraacetic acid) may be used as a titrant 140 and an indicator 136 (may be used to titrate a water sample 101. The procedure involves adding a known concentration of EDTA to the sample until the indicator changes color, indicating the end of the titration. The amount of EDTA used is then calculated as the total hardness, typically expressed as mg/L of calcium carbonate ($CaCO_3$). An amount of buffer solution 138 may be added automatically to the reaction chamber receptacle 130. The indicator is added to the receptacle 130 and the analyte solution 160 will change color if hardness is present. The color sensor 132 will sense this and record the point in time when the color changes and can stop the titration process of adding titrant 140 to the analyte solution 160 held in the reaction chamber receptacle 130. The total hardness reading/data value (e.g. 706) may be calculated using the following formula:

Total Hardness (mg/L as $CaCO_3$)=(Volume of EDTA used*Molarity of EDTA*Molecular weight of CaCO3)/(Volume of water sample).

To determine nitrite levels as a metric 112 through titration using the titration testing device 102, a sample 101 held in the reaction chamber receptacle 130 is treated with a standard oxidizing agent, typically potassium permanganate, in an acidic environment. The nitrite is oxidized to nitrate. The endpoint 142 of the titration is signaled by the persistence of a faint pink color, indicating that the oxidizing agent is in excess. The amount of titrant used is directly related to the nitrite concentration in the sample. The nitrite concentration can be calculated using the stoichiometry of the reaction and the volume of the titrant used, along with its concentration, and the sample volume.

To determine sulfite levels as a metric 112 through titration using the titration testing device 102, a sample 101 held in the reaction chamber receptacle 130 is To determine the sulfite level in a sample using titration, a standard solution of iodide-iodate or potassium iodate is added to the acidified sample, typically done using acid starch indicator, 101, which will react with the sulfite, oxidizing it to sulfate. The endpoint 142 of the titration is signaled by the appearance of a blue to purple color due to the reaction of free iodine with a starch indicator. To calculate the sulfite level, the exact volume of the potassium iodide-iodate solution has to be recorded that is used to reach the blue endpoint. The amount of sulfite in the sample can be calculated based on the volume of potassium iodide-iodate solution used and the known concentration of the titrant. The appropriate formula may then be used, which will depend on the specific titrant and sample volume, to determine the sulfite concentration in the sample 101. These calculations may all be performed automatically via the microcontroller 122 and/or the processing unit 902 of the computing device 108. The titration module 108 works with the microcontroller 122 and the titration testing device 102 to programmatically add any element needed including, but not limited to, buffer solution 138, titrant 140, indicator 136, or other chemical elements contained in solutions and/or containers that are in fluid communication with the reaction chamber 126 depending on the metric 112 that the user selected via the titration testing module 108 on the computing device 106 is being tested for. The added chemical elements will be added based on the sample test type selected (e.g. 110*a*-110*h* as shown in FIG. 5 in a non-limiting example by the user and the metric to be tested (e.g. metrics 112*a*-112*e* as shown in FIG. 5)

Chloride levels, as a metric 112, can be determined using titration via the titration testing device 102, silver nitrate may be used as a titrant 140 and silver chromate as an indicator dye. This titrant 140 (e.g. silver nitrate) is added from a burette to the reaction chamber receptacle 130 slowly while stirring the analyte solution 160. The color sensor 132 will observe and sense when a color change occurs in order for the titrant 140 to stop being added to the analyte solution 160. For example, when a red-brown precipitate of silver chromate forms, indicating that all chloride ions have reacted with the silver nitrate. The final volume of silver nitrate is added and recorded.

The concentration of chloride ions can be calculated using the following formula: Concentration of Chloride ($Cl^-$)= (Volume of AgNO3 used*Concentration of AgNO3)/Volume of sample.

Notably, the titration testing module 108 and/or the titration testing device 102 include a processing unit (e.g. 122 and 904) that can access the pre-programed formulas and calculations to calculate the specific metrics 112 by recording volumes and concentrations and amounts of any titrants 140 added and/or the original sample 101 volume and concentration when an endpoint 142 is detected or achieved. The automated titration testing device 102 combined with the titration testing module 108 is intended to replace the manual calculations a skilled or unskilled technician has to perform on multiple samples 101 to obtain the valuable data for these important metrics 112.

FIG. 6 shows an example of an interface or window 600 that includes one or more options in a drop down menu 604 for selectable, pre-programmed tests 110. Sample names 602 may be assigned to each sample and these interfaces may be included in the titration testing module 108 for a technician to track and follow the titration testing of a particular sample and any recorded data results that will be associated with the titration testing module 108.

FIG. 7 shows an exemplary table 700 that includes several data values 706 or readings that were processed and determined by the microcontroller 122 and/or processing unit 904 of the computing device 108 after titration testing was completed on a particular sample 101 via the automated titration testing device 102.

The table 700 may include one or more rows 702 and/or columns 704, whereby the metrics 112 of interest are listed on one side and the data values 706 along with the test type names 110 may be displayed on the table 700 as well. In this manner, the titration testing module 108 operates in conjunction with the titration testing device 102 to produce tangible reports 114 and/or tables that can be stored indefinitely and accessed over time as needed by a facility 103 or a technician monitoring the water/fluid at the facility or site 103.

Notably, in addition to the reports 114, the titration testing module 108 may include troubleshooting instructions 117 and recommended actions. For example, if sulfite in the boiler is below the normal recommended range of 30-60 ppm. Sulfite is an oxygen scavenger that serves to protect the boiler from corrosion, and low residuals lead to an increased risk of accelerated corrosion rates. Corrosion leads to reduced equipment life, failures and loss of efficiency. Potential causes are the chemical pump has lost prime, a change in makeup water quality, reduced feedwater temperatures or pressures, malfunctioning feedwater heaters, cold condensate return, and chemical contaminants from the condensate return or feedwater train. The troubleshooting instructions 117 from the module 108 may read for example "take the following troubleshooting steps. A) Ensure the chemical pump is primed B) Check feedwater for reduced temperatures C) Verify for proper functioning of the feedwater heater D) Increase pump stroke/speed settings or feed timers to increase the sulfite residual." Accordingly, these steps may help a technician determine how to return the elements (e.g. sulfite) in the water/fluid contained at the source site 103 at optimum levels.

Figure 8:
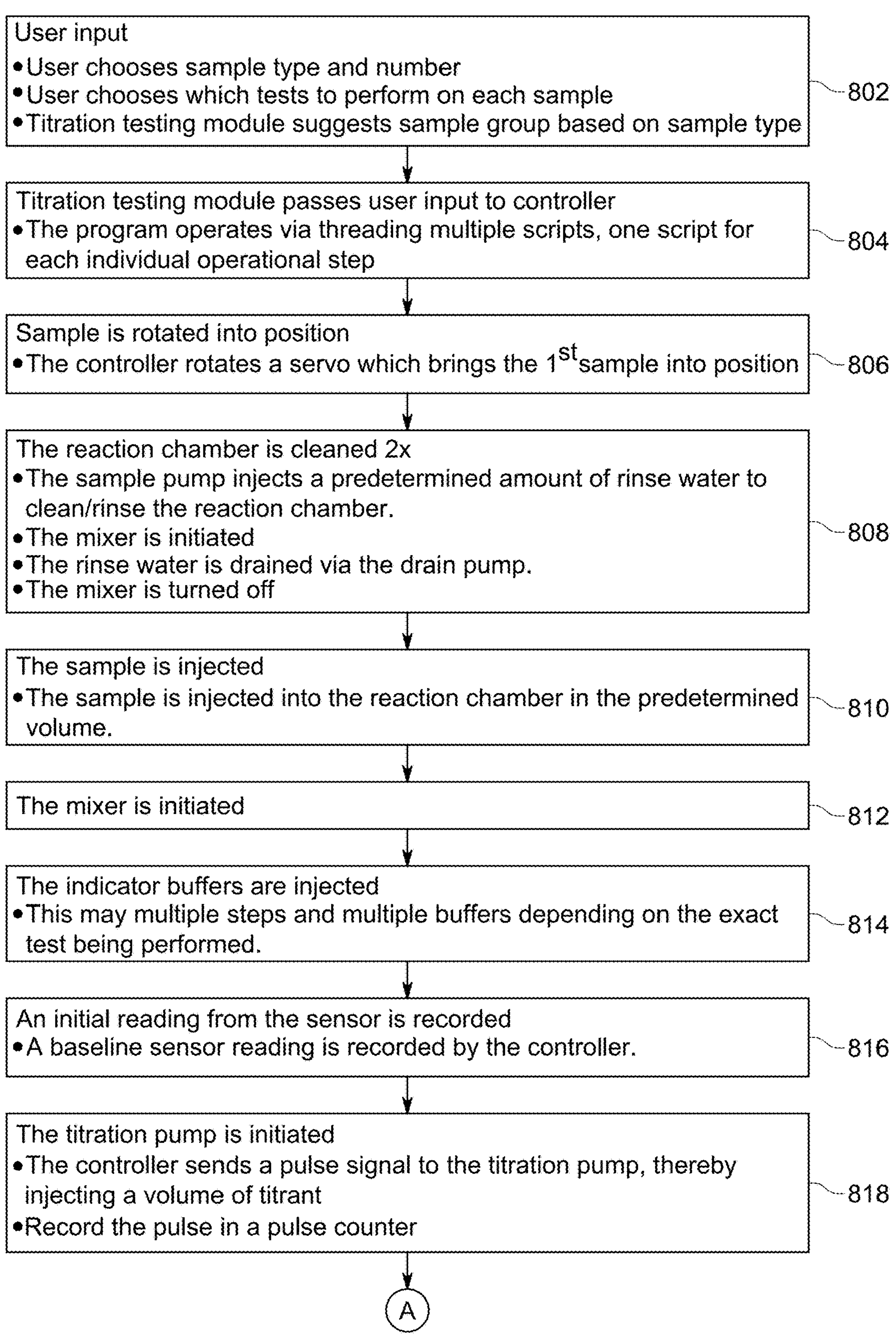
FIG. 8 is an exemplary flowchart with an exemplary method of using the automatic titration testing device and titration testing module on a computing device.
Figure 8:
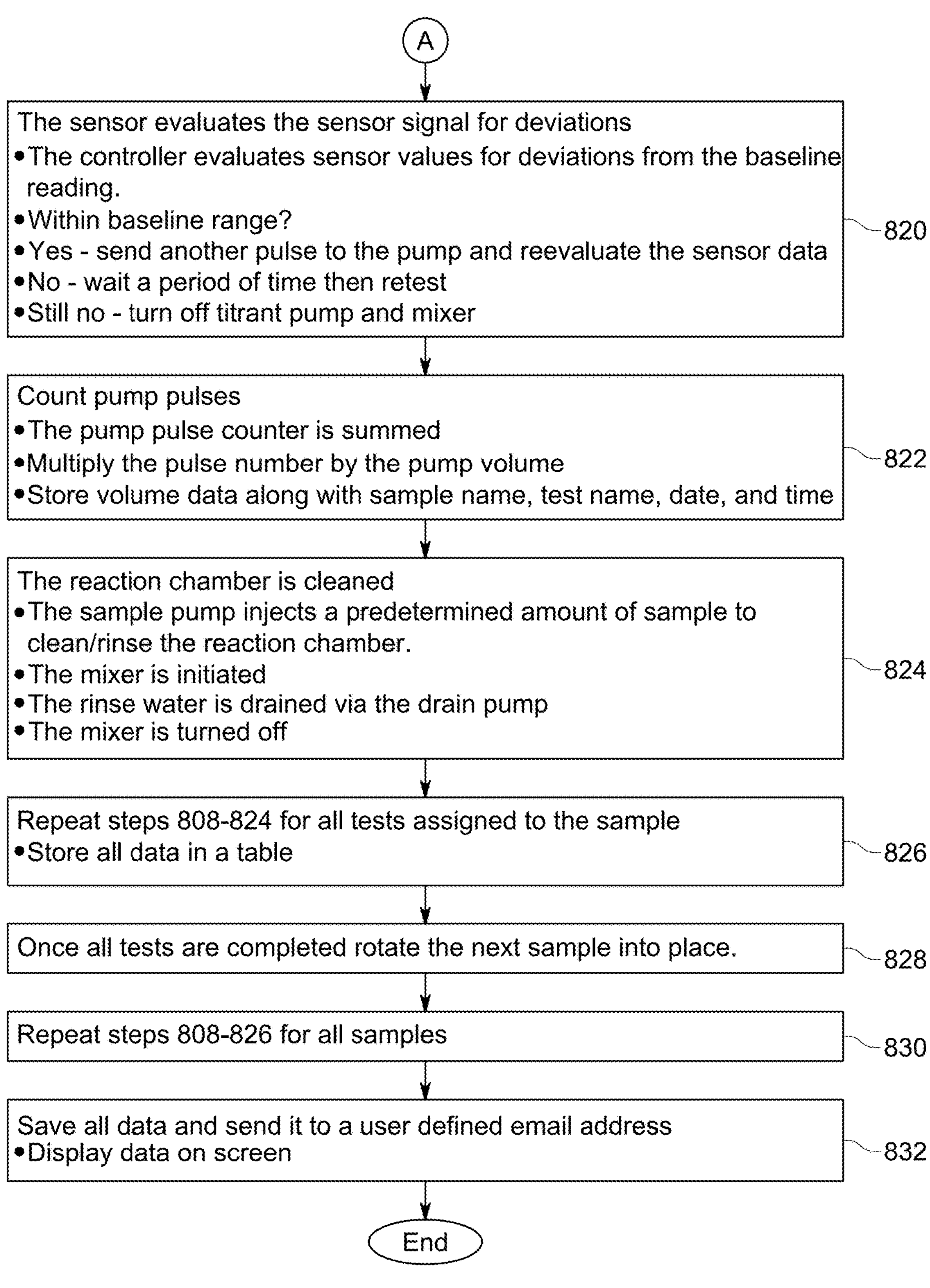

FIG. 8 provides an exemplary flowchart for using the automated testing device 102 as well as the titration testing module 108 as stored in the computing device 102. In a non-limiting embodiment, the process may begin with step 802, in which the technician or user (e.g. user 903 in FIG. 9) chooses which sample type and number. Based on the sample type the user will be presented with pre-programmed suggestions for analytes in which they are able to choose to proceed with the recommended tests or choose their own. The titration testing module 108 may include one or more interfaces and prompts and suggestions that suggest automatically a sample group based on sample type. In a non-limiting embodiment, the user may choose the sample testing type 110 for each sample 101 placed in the carousel 116 in a sample bottle 118. The user may be presented with a list of recommended tests for each sample bottle 118 holding the sample 101 obtained from elsewhere (e.g. source site 103), which the user can accept completely or modify based on their own needs by unchecking the set of metrics (e.g. metrics 112*a*-112*e* or the like) that the user does not need to analyze and test the sample contained in a particular sample bottle 118 on the carousel 116 for.

At step 804, as shown in the flowchart of FIG. 8, the titration testing module 108 passes along the user input to the microcontroller 122 of the titration testing device 102. The titration testing module 108 may operate via threading multiple scripts, such as one script for each individual operation step in a non-limiting embodiment.

At step 806, a sample 101 held in the sample bottle 118 is rotated into position by the carousel 116 to the pump suction intake line 402, for example, as shown in FIG. 4. There may be an airtight lid assembly 300 that is lowered into place onto the selected sample bottle 118 for testing and as noted above, this may ensure no additional contamination of the sample fluid 101 can occur and that the sample fluid 101 is pumped to the reaction chamber receptacle 130 in an airtight manner from the carousel 116 and from the sample bottle 118. The microcontroller 122 may further rotate a servomotor or motor 120 that brings the first sample bottle 118 into position beneath the pump suction intake line 402.

At step 808, in a non-limiting embodiment, the reaction chamber 126 and/or reaction chamber receptacle 130 is cleaned one or more times. A pump 124 may inject a predetermined amount of wash water/rinse water 128 into the reaction storage chamber receptacle 130 to clean and rinse out the receptacle 130. A mixer 150 is automatically initiated to mix the wash water in the receptacle 130 and then drained via one or more drain pumps (e.g. a pump 124). The mixer 150 may be automatically turned off. The microcontroller 122 may control the mixer 150 to turn on and off.

At step 810, the sample fluid 101 may be pumped from the sample bottle 118 on the carousel 116 and injected with a predetermined, known volume into the reaction chamber receptacle 130. At step 812, the microcontroller 122 may automatically initiate the mixer 150 again. At step 814, in some cases, the indicator buffers are injected into the reaction chamber receptacle 130 with the known volume of sample fluid 101 to be tested. Depending on the exact test 110 being performed and the metric 112 tested for, this step may involve multiple substeps and multiple buffers depending on the exact test 110 being performed. The titration testing module 108 will provide instructions to the titration testing device 102 as to how much of the indicator buffers to be added before the titrant 140 is added.

At step 816, an initial reading from the color sensor 132 is recorded. A baseline sensor reading is recorded by the microcontroller 122. The indicator dye 136 causes the sample water 101 pumped from the carousel 116 to the reaction chamber receptacle 130 to change color from clear to the color the buffer solution 138 is. This step may be very useful because the microcontroller 122 is looking for a change from the starting color and is not necessarily looking for a final color. To rephrase it, this step takes the baseline reading for the color sensor 132 and the machine 102 will add titrant 140 until the color values change by a certain percentage which then stops the titration.

At step 818, a titrant pump associated with the titrant 140 is initiated. The controller 122 may send a pulse signal to the pump driver 180 which then sends the correct voltage and wave shape to the titrant pump 124, thereby injecting a specific volume of titrant 140 slowly into the analyte solution 160 that is stored or held in the reaction chamber receptacle 130 within the reaction chamber 126. The pulse counter 144 is activated as well to record the pulses or drops of titrant 140 as the titrant 140 is slowly added to the reaction chamber receptacle 130.

At step 820, the color sensor 132 evaluates the sensor signal for deviations. The controller 122 may evaluate sensor values for deviations from the baseline reading and make a determination whether the system 100 is within baseline range. If the answer is yes, then another pulse is sent to the titrant pump to add more titrant 140 and the sensor data is re-evaluated. If no, then a period of time is allowed to pass and re-testing occurs. If still no, then the titrant pump is turned off along with the mixer 150.

At step 822, the pulse counter 144 sums up the number of pulses counted. Then calculations may be performed to calculate each metric 112 as specified by the titration testing module 108. The pulse number may be multiplied by the pulse volume. The volume data may be stored along with the sample name, test name, date and time etc.

At step 824, the reaction chamber receptacle 130 may be cleaned again with rinse water 128 and drained via a pump to prepare for another testing.

At step 826, steps 808-824 may be repeated for all tests assigned to a sample set 101. All data and values may be stored and displayed on one or more tables (e.g. 700 as shown in FIG. 7) and/or viewable or downloadable reports 114 via the titration testing module 108 on the computing device 106.

At step 828, once all tests are completed for any given sample, the carousel 116 rotates to the next sample bottle 118 in place and steps 808-828 repeated as well. As shown at step 832, the information may all be saved and emailed or sent to users/technicians in a manner that makes the data readily available and accessible and saves the technician time and provides better accuracy with respect to the titration testing process. Many times, a technician may have to perform 30 or more tests on a set of samples so using the titration testing device 102 and module 108 will greatly free up the time and effort a technician has to spend on the titration testing process to obtain the relevant data and metrics 112 to be obtained for the samples 101.

Turning to FIG. 9, FIG. 9 illustrates an exemplary system for one or more computing devices and the various exemplary components that may be employed in practicing one or more non-limiting embodiments of the invention as described herein. User computing device 106 may be any type of computing device known or to be created in the future. This may include, without limitation, fixed in place computers, such as desktop computers, or mobile computing devices. Mobile computing devices may include, but are not limited to, laptop computers, smartphones, mobile phones, tablets, wearable electronic computing devices or wearable devices.

FIG. 9 provides a schematic illustration of one embodiment of a computing device 106 that can perform the methods provided by the various other listed embodiments, as described herein, and/or can function as the host computer system, a remote kiosk/terminal, a point-of-sale device, a mobile device, a set-top box and/or a computer system. FIG. 9 is meant only to provide a generalized illustration of various components, any or all of which may be utilized as appropriate. FIG. 9 therefore, broadly illustrates how individual system elements may be implemented in a relatively separated or relatively more integrated manner.

In one or more embodiments, computing device 106 is in communication with one or more networks, such as network 115. Network 104 may include a local area network (LAN), such as a company Intranet, a metropolitan area network (MAN), or a wide area network (WAN), such as the Internet or World Wide Web. Network 104 may be a private network, a public network, or a combination thereof. Network 104 may be any type of network known in the art, including a telecommunications network, a wireless network (including Wi-Fi), and a wireline network. Network 104 may include mobile telephone networks.

The computing device 106 is shown comprising hardware elements that can be electrically coupled via a bus 902 (or may otherwise be in communication, as appropriate). The hardware elements of computing device 101 may include one or more processors 904, including without limitation one or more general-purpose processors and/or one or more special-purpose processors (such as digital signal processing chips, graphics acceleration processors, and/or the like). Computing device 106 may further include one or more input devices 908, which can include without limitation one or more cameras, sensors (including inertial sensors), a mouse, a keyboard and/or the like. In addition to the above, computing device 106 may include one or more output devices 910 such as the device display. Furthermore, in some embodiments, an input device 908 and an output device 910 of computing device 106 may be integrated, for example, in a touch screen or capacitive display as commonly found on mobile computing devices as well as desktop computers and laptops.

The computing device 106 may further include (and/or be in communication with) one or more non-transitory storage devices 906, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including without limitation, various file systems, database structures, and/or the like. Device storage may be used in a number of embodiments discussed herein. Further, the storage devices 906 may be non-volatile data storage devices in one or more non-limiting embodiments. Further, computing device 106 may be able to access removable nonvolatile storage devices 906 that can be shared among two or more information handling systems (e.g., computing devices) using various techniques, such as connecting the removable nonvolatile storage device 906 to a USB port or other connector of the information handling systems.

The computing device 106 might also include a communications subsystem 912, which can include without limitation a modem, a network card (wireless or wired), an infrared communication device, a wireless communication device and/or chipset (such as a Bluetooth™ device, an 802.11 device, a Wi-Fi device, a WiMax device, cellular communication facilities, etc.), and/or the like. The communications subsystem 912 may permit data to be exchanged with a network (e.g., such as network 115), other computer systems, and/or any other devices. In many embodiments, the computer system 0 will further comprise a non-transitory memory 914, which can include a RAM or ROM device, as described above.

The computing device 106 also can comprise software elements, shown as being currently located within the memory 914, which in some instances may including an operating system 916, device drivers, executable libraries, and/or other code, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer). In an aspect, then, such code and/or instructions can be used to configure and/or adapt computing device 106 to perform one or more operations in accordance with the described methods.

A set of these instructions and/or code might be stored on a computer-readable storage medium, such as the storage device(s) 906 described above. In some cases, the storage medium might be incorporated within a computer system, such as computing device 106. In other embodiments, the storage medium might be separate from computing device 106 (e.g., a removable medium, such as a compact disc or USB stick), and/or provided in an installation package, such that the storage medium can be used to program, configure, and/or adapt a general purpose computer with the instructions/code stored thereon. These instructions might take the form of executable code, which is executable by the computing device 106 and/or might take the form of source and/or installable code, which, upon compilation and/or installation on the computing device 106 (e.g., using any of a variety of generally available compilers, installation programs, compression/decompression utilities, etc.) then takes the form of executable code.

Some embodiments may employ a computer system (such as the computing device 106) to perform methods in accordance with the disclosure. For example, some or all of the procedures of the described methods may be performed by the computing device 106 in response to one or more processors 904 executing one or more sequences of one or more instructions (which might be incorporated into the operating system 916 and/or other code contained in the memory 914). Such instructions may be read into the memory 914 from another computer-readable medium, such as one or more of the storage device(s) 906. Merely by way of example, execution of the sequences of instructions contained in the memory 914 might cause the one or more processors 104 to perform one or more procedures of the methods described herein.

The terms "machine-readable medium" and "computer-readable medium," as used herein, refer to any medium that participates in providing data that causes a machine to operate in a specific fashion. In an embodiment implemented using the computing device 106, various computer-readable media might be involved in providing instructions/code to the one or more processors 904 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media may include, for example, optical and/or magnetic disks, such as the storage device(s) 906. Volatile media include, without limitation, dynamic memory, such as the memory 914. Transmission media may include, without limitation, coaxial cables, copper wire and fiber optics, including the wires that comprise the bus 902, as well as the various components of the communications subsystem 912 (and/or the media by which the communications subsystem 912 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a floppy disk, a flexible disk, hard disk, magnetic tape, or any other magnetic medium, a CD-ROM, any other optical medium, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to the processor(s) 904 for execution. Merely by way of example, the instructions may initially be carried on a magnetic disk and/or optical disc of a remote computer.

The communications subsystem 912 (and/or components thereof) generally will receive the signals, and the bus 902 then might carry the signals (and/or the data, instructions, etc. carried by the signals) to the memory 914, from which the one or more processors 904 retrieves and executes the instructions. The instructions received by the memory 914 may optionally be stored on a non-transitory storage device 906 either before or after execution by the processor(s) 204.

In one or more non-limiting embodiments, a computing device, such as computing device 106 may include a web browser such as web browser 923.

In one or more non-limiting embodiment, titration testing module 108 may be a software program or module that can be configured to allow a user to access testing of samples 101 and view recorded, obtained data regarding recommended sample tests 110 and metrics 112 obtained from the titration testing device 102.

In one or more non-limiting embodiments, titration testing module 108 may be implemented as a downloadable program or application storable on user computing device 106 for easy accessibility and viewability in one or more non-limiting embodiment.

In one or more non-limiting embodiments, hosting system 928 may be a cloud-based type hosting system. "Cloud-based" is a term that refers to applications, services, or resources made available to users on demand via a network, such as network 115, from a cloud computing provider's server, such as cloud-based server 932. Administrative entity 942 may be the cloud computing provider and may use servers 932 to provide access to data storage 934 and other systems that work in conjunction with the operation and maintenance of the titration testing module 108.

Hosting system 928 may include data storage systems 934 that can provide access to stored data by applications running on computing devices, such as computing device 106, that may be geographically separate from each other, provide offsite data backup and restore functionality, provide data storage to a computing device with limited storage capabilities, and/or provide storage functionality not implemented on computing device 106.

The hosting system 928 can be implemented such that client applications (for example, executing on computing device 106) can store, retrieve, or otherwise manipulate data objects in the hosting system 928. The hosting system 928 can be implemented by one or more server devices 932, which may be cloud-based server devices, which can be implemented using any type of computing device.

In one or more non-limiting embodiments, administrative entity 942 is the provider and creator of the titration testing module 108. Administrative entity 942 may make titration testing module 108 available to any client or user, such as user 903, who wants to use the titration analysis features of titration testing module 108. Administrative entity 942 may be able to manipulate and alter titration testing module 108 remotely so as to affect the operation and maintenance of the module 108 on server(s) 932 and as stored on one or more data storage devices 934 that are part of the hosting system 928. While administrative entity 942 is depicted as a single element communicating over network 115 and through the hosting system 928, it is noted that administrative entity 942, in one or more non-limiting embodiments, may be distributed over network 115 in any number of physical locations.

The user 903 may obtain samples 101 from the fluid source site 103 and utilize the testing module 108 to test via titrations the fluid samples 101 using the titration testing device 102. The titration testing device 102 may be connected wirelessly to the computing device 108 over a network 115 and/or via wires or a direct physical connection.

Titration testing module 108 may be stored on computing device 108 may also be stored or otherwise accessible by one or more servers 932 over network 115 by any party. The storage devices 906 may include a non-transitory computer readable medium including instructions, which when executed by a computer or processor (such as processors 904) may cause the computer or processor to perform operations to implement titration testing module 108.

Specific details are given in the description to provide a thorough understanding of the embodiments. However, embodiments may be practiced without these specific details. For example, well-known circuits, processes, algorithms, structures, and techniques have been shown without unnecessary detail, in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Also, some embodiments are described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Further, processors 904 of computing device 106 may perform the associated tasks.

Advantageously, the titration testing device 102 helps to free up technicians/user's time. The titration testing device 102 provides real-time data that can be stored and visible on the titration testing module on a computing device 106. The titration testing device 102 provides increased accuracy, efficiency, and enhanced repeatability of the test results as compared to manual methods. Further, the ability to extract the volumes and utilize the volumes for formulas and calculations of the metrics 112 provides better data analysis. Additionally, the system 100 offers troubleshooting instructions 117 and solutions when detecting that a metric 112 is out of range or below a desired minimum level. Other advantages and benefits are also provided by the system 100 as described herein and as shown in one or more non-limiting embodiments in the accompanying figures.

References in the singular tense include the plural, and vice versa, unless otherwise noted. The term "set" as used herein may refer to one or more items. The term "coupled to" as used herein may refer to items connected via direct or indirect means. Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof.

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, among others, are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm and upper limit is 100 mm.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. A water-sample titration testing system, comprising:

a water sample handling subsystem comprising:

a carousel configured to hold a plurality of sample bottles containing water samples, and a carousel drive motor operable to move the carousel to position a selected sample bottle of the plurality of sample bottles;

a fluidic transfer subsystem comprising:

one or more sample pumps configured to draw a measured amount of a selected water sample from the selected sample bottle, and a reaction chamber receptacle configured to receive the measured amount of the selected water sample from the selected sample bottle;

a mixing subsystem comprising a mixer configured to agitate fluid within the reaction chamber receptacle during a titration procedure;

a reagent delivery subsystem comprising:

a titrant delivery mechanism configured to dispense a titrant into the reaction chamber receptacle, and a plurality of indicator dye containers each holding a respective indicator dye, and one or more indicator pumps configured to selectively deliver a particular indicator dye from a selected one of the plurality of indicator dye containers into the reaction chamber receptacle;

an optical sensing subsystem comprising a color sensor positioned to detect a color characteristic of the fluid within the reaction chamber receptacle;

a controller subsystem comprising:

a microcontroller operatively coupled to the carousel drive motor, the one or more sample pumps, the mixer, the titrant delivery mechanism, the one or more indicator pumps, and the color sensor; and a computing device executing a titration testing module that provides a user interface for selecting a test metric for the selected water sample;

wherein the titration testing module stores a plurality of pre-programmed test profiles, each pre-programmed test profile corresponding to a respective metric and specifying at least (a) a titrant type and (b) an indicator dye type;

wherein the titration testing module is configured to automatically perform, for each of the plurality of the water samples held in the plurality of sample bottles on the carousel, a selected set of the pre-programmed test profiles to determine a plurality of titration results corresponding to a plurality of test metrics, wherein the titration testing module causes the microcontroller to sequentially position different sample bottles from the plurality of sample bottles and execute the selected set of pre-programmed test profiles;

and wherein the titration testing module is configured to calculate, for each of the water samples, metric values for the plurality of test metrics based on stored titration results, and to display test metric values in a table on a display of the computing device;

wherein, in response to selection of a test metric of the plurality of test metrics via the user interface, the titration testing module causes the microcontroller to:

(i) actuate the carousel drive motor to position the selected sample bottle;

(ii) actuate a sample pump of the one or more sample pumps to transfer the measured amount of the selected water sample into the reaction chamber receptacle;

(iii) actuate an indicator pump of the one or more indicator pumps to deliver the particular indicator dye from the one or more indicator dye containers corresponding to the test metric into the reaction chamber receptacle;

(iv) actuate the mixer to mix the selected water sample and the particular indicator dye;

(v) actuate the titrant delivery mechanism to dispense the titrant into the reaction chamber receptacle while the color sensor generates sensor data representing a detected color characteristic; and (vi) determine, based on the sensor data, a titration based result corresponding to the test metric and store the titration based result in memory for display in the table.

2. The system of claim 1, wherein the plurality of test metrics comprise pH, p-alkalinity, total hardness, calcium hardness, chloride level, sulfite level, nitrite level, conductivity, corrected conductivity, m-alkalinity, OH-alkalinity, phosphate level, or phosphonate level.

3. The system of claim 1, further comprising, a lid assembly having a lid, a tube, a one way check valve, and a gasket seal wherein the lid is coupled to the tube and the one way check valve and the gasket seal is coupled or attached to a top surface of the lid.

4. The system of claim 3, wherein the lid assembly is automatically positioned onto the selected sample bottle before pumping the selected water sample to the reaction chamber receptacle.

5. The system of claim 3, wherein an airtight nozzle is positioned on the gasket seal of the lid.

6. The system of claim 1, further comprising, a self-calibrating pH probe and a self-calibrating conductivity probe.

7. The system of claim 1, wherein an endpoint is sensed by the color sensor after the titration procedure has started.

8. The system of claim 1, further comprising, an effluent pump, wherein an analyte solution stored in the reaction chamber receptacle is pumped out of the reaction chamber receptacle by the effluent pump upon conclusion of testing.

9. The system of claim 1, further comprising, a clean water source wherein the clean water source provides water that is pumped to the reaction chamber receptacle before a new titration occurs.

* * * * *